(12) United States Patent
Flaherty et al.

(10) Patent No.: US 7,991,461 B2
(45) Date of Patent: Aug. 2, 2011

(54) PATIENT TRAINING ROUTINE FOR BIOLOGICAL INTERFACE SYSTEM

(75) Inventors: J. Christopher Flaherty, Topsfield, MA (US); Mijail D. Serruya, Providence, RI (US); Daniel S. Morris, Stanford, CA (US); Abraham H. Caplan, Cambridge, MA (US); Maryam Saleh, Chicago, IL (US); John P. Donoghue, Providence, RI (US)

(73) Assignee: BrainGate Co., LLC, Ponte Vedra Beach, FL (US)

( * ) Notice: Subject to any disclaimer, the term of this patent is extended or adjusted under 35 U.S.C. 154(b) by 1506 days.

(21) Appl. No.: 11/315,225

(22) Filed: Dec. 23, 2005

(65) Prior Publication Data

US 2006/0167530 A1     Jul. 27, 2006

Related U.S. Application Data

(60) Provisional application No. 60/642,021, filed on Jan. 6, 2005.

(51) Int. Cl.
*A61B 5/04*     (2006.01)
(52) U.S. Cl. ........................ 600/545; 600/544
(58) Field of Classification Search .................. 600/545; 623/25
See application file for complete search history.

(56) References Cited

U.S. PATENT DOCUMENTS

| | | |
|---|---|---|
| 3,837,339 A | 9/1974 | Aisenberg et al. |
| 3,850,161 A | 11/1974 | Liss |
| 4,055,175 A | 10/1977 | Clemens et al. |
| 4,146,029 A | 3/1979 | Ellinwood, Jr. |
| 4,294,245 A | 10/1981 | Bussey |
| 4,360,031 A | 11/1982 | White |
| 4,461,304 A | 7/1984 | Kuperstein |
| 4,566,464 A | 1/1986 | Piccone et al. |
| 4,569,352 A | 2/1986 | Petrofsky et al. |
| 4,633,889 A | 1/1987 | Talalla et al. |
| 4,690,142 A | 9/1987 | Ross et al. |
| 4,837,049 A | 6/1989 | Byers et al. |
| 4,865,048 A | 9/1989 | Eckerson |

(Continued)

FOREIGN PATENT DOCUMENTS

EP     0 911 061 A     4/1999

(Continued)

OTHER PUBLICATIONS

Kensall D. Wise et al., "An Integrated-Circuit Approach to Extraceullar Microelectrodes," IEEE Transactions on Biomedical Engineering, vol. BME-17, No. 3, Jul. 1970, pp. 238-247.

(Continued)

*Primary Examiner* — Patricia C Mallari
(74) *Attorney, Agent, or Firm* — SoCal IP Law Group LLP; Steven C. Sereboff; M. Kala Sarvaiya

(57) ABSTRACT

Various embodiments of a biological interface system and related methods are disclosed. The system may comprise a sensor comprising a plurality of electrodes for detecting multicellular signals emanating from one or more living cells of a patient and a processing unit configured to receive the multicellular signals from the sensor and process the multicellular signals to produce a processed signal. The processing unit may be configured to transmit the processed signal to a controlled device that is configured to receive the processed signal. The system is configured to perform an integrated patient training routine to generate one or more system configuration parameters that are used by the processing unit to produce the processed signal.

37 Claims, 5 Drawing Sheets

U.S. PATENT DOCUMENTS

| | | | |
|---|---|---|---|
| 4,878,913 A | 11/1989 | Aebischer et al. | |
| 4,883,666 A | 11/1989 | Sabel et al. | |
| 4,969,468 A | 11/1990 | Byers et al. | |
| 5,037,376 A | 8/1991 | Richmond et al. | |
| 5,081,990 A | 1/1992 | Deletis | |
| 5,092,329 A | 3/1992 | Graupe et al. | |
| 5,112,296 A | 5/1992 | Beard et al. | |
| 5,119,832 A | 6/1992 | Xavier | |
| 5,156,844 A | 10/1992 | Aebischer et al. | |
| 5,215,088 A | 6/1993 | Normann et al. | |
| 5,325,862 A | 7/1994 | Lewis et al. | |
| 5,325,865 A | 7/1994 | Beckman et al. | |
| 5,361,760 A | 11/1994 | Normann et al. | |
| 5,413,611 A | 5/1995 | Haslam et al. | |
| 5,423,877 A | 6/1995 | Mackey | |
| 5,445,608 A | 8/1995 | Chen et al. | |
| 5,458,631 A | 10/1995 | Xavier | |
| 5,474,082 A | 12/1995 | Junker | |
| 5,474,547 A | 12/1995 | Aebischer et al. | |
| 5,549,656 A | 8/1996 | Reiss | |
| 5,617,871 A | 4/1997 | Burrows | |
| 5,638,826 A | 6/1997 | Wolpaw et al. | |
| 5,687,291 A | 11/1997 | Smyth | |
| 5,692,517 A | 12/1997 | Junker | |
| 5,697,951 A | 12/1997 | Harpstead et al. | |
| 5,702,432 A | 12/1997 | Chen et al. | |
| 5,713,923 A | 2/1998 | Ward et al. | |
| 5,724,987 A | 3/1998 | Gevins et al. | |
| 5,735,885 A | 4/1998 | Howard, III et al. | |
| 5,748,845 A | 5/1998 | Labun et al. | |
| 5,758,651 A | 6/1998 | Nygard et al. | |
| 5,797,898 A | 8/1998 | Santini, Jr. et al. | |
| 5,814,089 A | 9/1998 | Stokes et al. | |
| 5,843,093 A | 12/1998 | Howard, III | |
| 5,843,142 A | 12/1998 | Sultan | |
| 5,855,801 A | 1/1999 | Lin et al. | |
| 5,857,978 A | 1/1999 | Hively et al. | |
| 5,873,840 A | 2/1999 | Neff | |
| 5,928,228 A | 7/1999 | Kordis et al. | |
| 5,938,688 A | 8/1999 | Schiff | |
| 5,938,689 A | 8/1999 | Fischell et al. | |
| 5,938,690 A | 8/1999 | Law et al. | |
| 5,995,868 A | 11/1999 | Dorfmeister et al. | |
| 6,001,065 A | 12/1999 | DeVito | |
| 6,006,124 A | 12/1999 | Fischell et al. | |
| 6,016,449 A | 1/2000 | Fischell et al. | |
| 6,018,682 A | 1/2000 | Rise et al. | |
| 6,024,700 A | 2/2000 | Nemirovski et al. | |
| 6,024,702 A | 2/2000 | Iversen | |
| 6,027,456 A | 2/2000 | Feler et al. | |
| 6,038,477 A | 3/2000 | Kayyali | |
| 6,044,292 A | 3/2000 | Heyrend et al. | |
| 6,061,593 A | 5/2000 | Fischell et al. | |
| 6,086,582 A | 7/2000 | Altman et al. | |
| 6,091,015 A | 7/2000 | del Valle et al. | |
| 6,092,058 A | 7/2000 | Smyth | |
| 6,094,598 A | 7/2000 | Elsberry et al. | |
| 6,113,553 A | 9/2000 | Chubbuck | |
| 6,125,300 A | 9/2000 | Weijand et al. | |
| 6,128,538 A | 10/2000 | Fischell et al. | |
| 6,134,474 A | 10/2000 | Fischell et al. | |
| 6,154,678 A | 11/2000 | Lauro | |
| 6,161,045 A | 12/2000 | Fischell et al. | |
| 6,163,725 A | 12/2000 | Peckham et al. | |
| 6,169,981 B1 | 1/2001 | Werbos | |
| 6,171,239 B1 * | 1/2001 | Humphrey | 600/372 |
| 6,175,762 B1 | 1/2001 | Kirkup et al. | |
| 6,181,965 B1 | 1/2001 | Loeb et al. | |
| 6,185,455 B1 | 2/2001 | Loeb et al. | |
| 6,216,045 B1 | 4/2001 | Black et al. | |
| 6,224,549 B1 | 5/2001 | Drongelen | |
| 6,240,315 B1 | 5/2001 | Mo et al. | |
| 6,254,536 B1 | 7/2001 | DeVito | |
| 6,263,237 B1 | 7/2001 | Rise | |
| 6,280,394 B1 | 8/2001 | Maloney et al. | |
| 6,304,775 B1 | 10/2001 | Iasemidis et al. | |
| 6,309,410 B1 | 10/2001 | Kuzma et al. | |
| 6,313,093 B1 | 11/2001 | Frey, II | |
| 6,319,241 B1 | 11/2001 | King et al. | |
| 6,353,754 B1 | 3/2002 | Fischell et al. | |
| 6,354,299 B1 | 3/2002 | Fischell et al. | |
| 6,356,784 B1 | 3/2002 | Lozano et al. | |
| 6,358,202 B1 | 3/2002 | Arent | |
| 6,360,122 B1 | 3/2002 | Fischell et al. | |
| 6,366,813 B1 | 4/2002 | DiLorenzo | |
| 6,427,086 B1 | 7/2002 | Fischell et al. | |
| 6,436,708 B1 | 8/2002 | Leone et al. | |
| 6,459,936 B2 | 10/2002 | Fischell et al. | |
| 6,466,822 B1 | 10/2002 | Pless | |
| 6,473,639 B1 | 10/2002 | Fischell et al. | |
| 6,480,743 B1 | 11/2002 | Kirkpatrick et al. | |
| 6,549,804 B1 | 4/2003 | Osorio et al. | |
| 6,577,893 B1 | 6/2003 | Besson et al. | |
| 6,620,415 B2 | 9/2003 | Donovan | |
| 6,636,763 B1 | 10/2003 | Junker et al. | |
| 6,658,287 B1 | 12/2003 | Litt et al. | |
| 6,920,359 B2 | 7/2005 | Meadows et al. | |
| 7,010,351 B2 | 3/2006 | Firlik et al. | |
| 7,206,632 B2 | 4/2007 | King | |
| 7,212,851 B2 | 5/2007 | Donoghue et al. | |
| 7,280,870 B2 | 10/2007 | Nurmikko et al. | |
| 7,346,396 B2 | 3/2008 | Barriskill et al. | |
| 7,392,079 B2 | 6/2008 | Donoghue et al. | |
| 2001/0014818 A1 | 8/2001 | Kennedy | |
| 2001/0023368 A1 | 9/2001 | Black et al. | |
| 2001/0027336 A1 | 10/2001 | Gielen et al. | |
| 2001/0029391 A1 | 10/2001 | Gluckman et al. | |
| 2001/0051819 A1 | 12/2001 | Fischell et al. | |
| 2001/0056290 A1 | 12/2001 | Fischell et al. | |
| 2002/0002390 A1 | 1/2002 | Fischell et al. | |
| 2002/0013612 A1 | 1/2002 | Whitehurst | |
| 2002/0016638 A1 | 2/2002 | Mitra et al. | |
| 2002/0077534 A1 | 6/2002 | DuRousseau | |
| 2002/0077620 A1 | 6/2002 | Sweeney et al. | |
| 2002/0082514 A1 | 6/2002 | Williams et al. | |
| 2002/0099412 A1 | 7/2002 | Fischell et al. | |
| 2002/0169485 A1 | 11/2002 | Pless et al. | |
| 2003/0004428 A1 | 1/2003 | Pless et al. | |
| 2003/0074032 A1 | 4/2003 | Gliner | |
| 2003/0082507 A1 | 5/2003 | Stypulkowski | |
| 2003/0083716 A1 | 5/2003 | Nicolelis et al. | |
| 2003/0083724 A1 | 5/2003 | Jog et al. | |
| 2003/0093129 A1 * | 5/2003 | Nicolelis et al. | 607/45 |
| 2003/0139782 A1 | 7/2003 | Duncan et al. | |
| 2003/0139783 A1 | 7/2003 | Kilgore et al. | |
| 2004/0006264 A1 | 1/2004 | Mojarradi et al. | |
| 2004/0073414 A1 | 4/2004 | Bienenstock et al. | |
| 2004/0138579 A1 | 7/2004 | Deadwyler et al. | |
| 2004/0193068 A1 | 9/2004 | Burton et al. | |
| 2004/0267320 A1 | 12/2004 | Taylor et al. | |
| 2005/0090756 A1 | 4/2005 | Wolf et al. | |
| 2005/0137652 A1 | 6/2005 | Cauller et al. | |
| 2005/0182341 A1 | 8/2005 | Katayama et al. | |
| 2005/0267597 A1 * | 12/2005 | Flaherty et al. | 623/24 |
| 2005/0273890 A1 | 12/2005 | Flaherty et al. | |
| 2005/0283203 A1 | 12/2005 | Flaherty et al. | |
| 2006/0029912 A1 | 2/2006 | Kearby et al. | |
| 2006/0049957 A1 | 3/2006 | Surgenor et al. | |
| 2006/0149338 A1 | 7/2006 | Flaherty et al. | |
| 2006/0167371 A1 | 7/2006 | Flaherty et al. | |
| 2006/0167530 A1 | 7/2006 | Flaherty et al. | |
| 2006/0173259 A1 | 8/2006 | Flaherty et al. | |
| 2006/0189900 A1 | 8/2006 | Flaherty | |
| 2006/0195042 A1 | 8/2006 | Flaherty | |
| 2006/0206167 A1 | 9/2006 | Flaherty et al. | |
| 2006/0241356 A1 | 10/2006 | Flaherty | |
| 2006/0253166 A1 | 11/2006 | Flaherty et al. | |
| 2007/0032738 A1 | 2/2007 | Flaherty et al. | |
| 2007/0156126 A1 | 7/2007 | Flaherty | |
| 2010/0023021 A1 | 1/2010 | Flaherty | |
| 2010/0063411 A1 | 3/2010 | Donoghue et al. | |

FOREIGN PATENT DOCUMENTS

| | | |
|---|---|---|
| WO | WO 01/43635 | 6/2001 |
| WO | WO 01/60445 | 8/2001 |
| WO | WO 01/78833 | 10/2001 |
| WO | WO 01/93756 A2 | 12/2001 |

| | | |
|---|---|---|
| WO | WO 02/093312 A2 | 11/2002 |
| WO | WO 02/100267 A1 | 12/2002 |
| WO | WO 03/026739 | 4/2003 |
| WO | WO 03/035165 | 5/2003 |
| WO | WO 03/037231 | 5/2003 |
| WO | WO 03/061465 A2 | 7/2003 |
| WO | WO 2006/044793 A2 | 4/2006 |

OTHER PUBLICATIONS

Donald R. Humphrey et al., "Predicting Measures of Motor Performance from Multiple Cortical Spike Trains," Science, New Series, vol. 170, Issue 3959, Nov. 13, 1970, pp. 758-762.

A. Bohg, "Ethylene Diamine-Pyrocatechol-Water Mixture Shows Etching Anomaly in Boron-Doped Silicon," Journal of the Electrochemical Society, vol. 118, No. 2, Feb. 1971, pp. 401-402.

Donald R. Humphrey, "Relating Motor Cortex Spike Trains to Measures of Motor Performance," Department of Physiology, Emory University, Brain Research, No. 40, 1972, pp. 7-18.

Arnold Starr et al., "An Evaluation of Photoengraved Microelectrodes for Extracellular Single-Unit Recording," IEEE Transactions on Biomedical Engineering, vol. BME-20, No. 4, Jul. 1973, pp. 291-293.

Kensall D. Wise et al., "A Low-Capacitance Multielectrode Probe for Use in Extracellular Neurophysiology," IEEE Transactions on Biomedical Engineering, vol. BME-22, No. 3, May 1975, pp. 212-219.

V. B. Mountcastle et al., "Posterior Parietal Association Cortex of the Monkey: Command Functions for Operations Within Extrapersonal Space," The Journal of Neurophysiology, vol. 38, No. 4, 1975, pp. 871-908.

Edward M. Schmidt, "Single Neuron Recording From Motor Cortex as a Possible Source of Signals for Control of External Devices," Annals of Biomedical Engineering, vol. 8, 1980, pp. 339-349.

A. J. S. Summerlee et al., "The effect of behavioural arousal on the activity of hypothalamic neurons in unanaesthetized, freely moving rats and rabbits," Proceedings of the Royal Society of London Series B-Biological Sciences, Jan. 1982, pp. 263-272.

Spencer L. BeMent, et al., "Solid-State Electrodes for Multichannel Multiplexed Intracortical Neuronal Recording," IEEE Transactions on Biomedical Engineering, vol. BME-33, No. 2, Feb. 1986, pp. 230-241.

Camilo Toro et al., "8-12 Hz rhythmic oscillations in human motor cortex during two-dimensional arm movements: evidence for representation of kinematic parameters," Departments of Neurology, Neurosurgery, and Physiology, University of Minnesota; MINCEP Epilepsy Care, P.A.; The Minessota Epilepsy Group of United and St. Paul Children's Hospital; and Human Motor Control Section, National Institute of Neurological Disorders and Stroke, National Institutes of Health, Electroencephalorapy and Clinical Neurophysiology, No. 93, 1994, pp. 390-403.

Anthony L. Owens et al., "Multi-electrode array for measuring evoked potentials from surface of ferret primary auditory cortex," Journal of Neuroscience Methods, vol. 58, Nos. 1/2, May 1995, pp. 209-220.

Miguel A. L. Nicolelis et al., "Sensorimotor Encoding by Synchronous Neural Ensemble Activity at Multiple Levels of the Somatosensory System," Science, vol. 268, Jun. 2, 1995, pp. 1353-1358.

Jerome N. Sanes et al., "Shared Neural Substrates Controlling Hand Movements in Human Motor Cortex," Science, vol. 268, Jun. 23, 1995, pp. 1775-1777.

D.M. Halliday et al., "A Framework for the Analysis of Mixed Time Series/Point Process Data-Theory and Application to the Study of Physiological Tremor, Single Motor Unit Discharges and Electromyograms," Progress in Biophysics Molecular Biology, vol. 64, Nos. 2/3, 1995, pp. 237-278.

Qing Bai et al., "A High-Yield Process for Three-Dimensional Microelectrode Arrays," Solid-State Sensor and Actuator Workshop, Hilton Head, South Carolina, Jun. 2-6, 1996, pp. 262-265.

Apostolos P. Georgopoulos et al., "Neuronal Population Coding of Movement Direction," Science, vol. 233, Sep. 26, 1986, pp. 1416-1419.

Kenneth L. Drake et al., "Performance of Planar Multisite Microprobes in Recording Extracellular Single-Unit Intracortical Activity," IEEE Transactions on Biomedical Engineering, vol. 35, No. 9, Sep. 1988, pp. 719-732.

Patrick K. Campbell et al., "A chronic intracortical electrode array: Preliminary results," Journal of Biomed. Material Res.: Applied Biomaterials, vol. 23, No. 2, 1989, pp. 245-259.

Andrew R. Mitz et al., "Learning-dependent Neuronal Activity in the Premotor Cortex: Activity during the Acquisition of Conditional Motor Associations," The Journal of Neuroscience, vol. 11, No. 6, Jun. 1991, pp. 1855-1872.

Patrick K. Campbell et al., "A Silicon-Based, Three-Dimensional Neural Interface: Manufacturing Processes for an Intracortical Electrode Array," IEEE Transactions, 1991, pp. 758-768.

A. C. Hoogerwerf et al., "A Three-Dimensional Neural Recording Array," IEEE Transactions, 1991, pp. 120-123.

Gregory T. A. Kovacs et al., "Regeneration Microelectrode Array for Peripheral Nerve Recording and Stimulation," Transactions on Biomedical Engineering, vol. 39, No. 9, Sep. 1992, pp. 893-902.

Kelly E. Jones et al., "A Glass/Silicon Composite Intracortical Electrode Array," Annals of Biomedical Engineering. vol. 20, 1992, pp. 423-437.

Miguel A. L. Nicolelis et al., "Induction of immediate spatiotemporal changes in thalamic networks by peripheral block of ascending cutaneous information," Letters to Nature, vol. 361, Feb. 11, 1993, pp. 533-536.

Reinhard Eckhom et al., "A new method for the insertion of multiple microprobes into neural and muscular tissue, including fiber electrodes, fine wires, needles and microsensors," Journal of Neuroscience Methods, vol. 49, Nos. 1/2, 1993, pp. 175-179.

Craig T. Nordhausen et al., "Optimizing recording capabilities of the Utah Intracortical Electrode Array," Brain Research, vol. 637, Nos. 1/2 , Feb. 21, 1994, pp. 27-36.

Jamille F. Hetke et al., "Silicon Ribbon Cables for Chronically Implantable Microelectrode Arrays," IEEE Transactions on Biomedical Engineering, vol. 41, No. 4, Apr. 1994, pp. 314-321.

Miguel A. L. Nicolelis et al., "Spatiotemporal Structure of Somatosensory Responses of Many-Neuron Ensembles in the Rat Ventral PosteriorMedial Nucleus of the Thalamus," The Journal of Neuroscience, vol. 14, No. 6, Jun. 1994, pp. 3511-3532.

Arnold C. Hoogerwerf et al., "A Three-Dimensional Microelectrode Array for Chronic Neural Recording," IEEE Transactions on Biomedical Engineering, vol. 41, No. 12, Dec. 1994, pp. 1136-1146.

Changhyun Kim et al., "A 64-Site Multishank CMOS Low-Profile Neural Stimulating Probe," IEEE Journal of Solid-State Circuits, vol. 31, No. 9, Sep. 1996, pp. 1230-1238.

Gwo-Ching Chang et al., "Real-time implementation of electromyogram pattern recognition as a control command of man-machine interface," Medical Engineering Phys., vol. 18, No. 7, 1996, pp. 529-537.

P. Nisbet, "intergrating assistive technologies: current practices and future possibilities," Med. Eng. Phys., vol. 18, No. 3, 1996, pp. 193-202.

Miguel A. L. Nicolelis et al., "Reconstructing the Engram: Simultaneous, Multisite, Many Sinle Neuron Recordings," Nueron, vol. 18, Apr. 1997, pp. 529-537.

TR Scott et al., "The Monitoring of Tendon Tension with an Implantable Intratendon Probe and Its Use in the Control of Neuroprostheses," IEEE Transactions on Rehabilitation Engineering, vol. 5, No. 2, Jun. 1997, pp. 233-235.

Barbara M. Faggin et al., "Immediate and simultaneous sensory reorganization at cortical and subcortical levels of the somatosensory system," Proc. Natl. Acad. Science USA, vol. 94, Aug. 1997, pp. 9428-9433.

Nicolelis, Miguel A.L., "Trigeminal System Plasticity During Facial Anethesia," Department of Health and Human Services, Public Health Service, Grant No. 2 RO1 DE11451-05, Including Summary Statement, Oct. 1997.

Robert M. Bradley et al., "Long term chronic recordings from peripheral sensory fibers using a sieve electrode array," Journal of Neuroscience Methods, vol. 73, 1997, pp. 177-186.

David K. Warland et al., "Decoding Visual Information From a Population of Retinal Ganglion Cells," The American Physiological Society, 1997, pp. 2336-2350.

Steven P. Wise et al., "Premotor and Parietal Cortex: Cortiococortical Connectivity and Combinatorial Computations," Annual Review of Neuroscience, vol. 20, 1997, pp. 25-42.

P.R. Kennedy et al., "Restoration of neural output from a paralyzed patient by a direct brain connection," NeuroReport, vol. 9, No. 8, Jun. 1998 pp. 1707-1711.

Paolo Dario et al., "Neural Interfaces for Regenerated Nerve Stimulation and Recording," IEEE Transactions on Rehabilitation Engineering, vol. 6, No. 4, Dec. 1998, pp. 353-363.

Nicholas G. Hatsopoulos et al., "Information about movement direction obtained from synchronous activity of motor cortical neurons," Proc. Natl. Acad. Sci. USA, vol. 95, Dec. 1998, pp. 15706-15711.

John P. Donoghue et al., "Neural Discharge and Local Field Potential Oscillations in Primate Motor Cortex During Voluntary Movements," The American Physiological Society, 1998, pp. 159-173.

Nicolelis, Miguel A.L., "Trigeminal System Plasticity During Facial Anethesia," Department of Health and Human Services, Public Health Service, Grant No. 2 R01 DE11451-06, Apr. 1999.

Gregor Rainer et al., "Prospective Coding for Objects in Primate Prefrontal Cortex," The Journal of Neuroscience, vol. 19, No. 13, Jul. 1, 1999, pp. 5493-5505.

John K. Chapin et al., "Real-time control of a robot arm using simultaneously recorded neurons in the motor cortex," Department of Neurobiology and Anatomy, MCP Hahnemann School of Medicine; and Department of Neurobiology, Duke University Medical Center, Nature Neuroscience, vol. 2, No. 7, Jul. 1999, pp. 664-670.

E. M. Maynard et al, "Neuronal Interactions Improve Cortical Population Coding of Movement Direction," The journal of Neuroscience, vol. 19, No. 18, Sep. 15, 1999, pp. 8083-8093.

F. Gandolfo et al., "Cortical correlates of learning in monkeys adapting to a new dynamical environment," PNAS, vol. 97, No. 5, Feb. 29, 2000, pp. 2259-2263.

J. F. Marsden et al., "Organization of Cortical Activities Related to Movement in humans," The Journal of Neuroscience, vol. 20, No. 6, Mar. 15, 2000, pp. 2307-2314.

D. Gareth Evans et al., "Controlling mouse Pointer Position Using an Infrared Head-Operated Joystick," IEEE Transaction on Rehabilitation Engineering, vol. 8, No. 1, Mar. 2000, pp. 107-117.

Qing Bai et al., "A High-Yield Microassembly Structure for Three-Dimensional Microelectrode Arrays," IEEE Transactions on Biomedical Engineering, vol. 47, No. 3, Mar. 2000, pp. 281-289.

Nicolelis, Miguel A.L., "Trigeminal System Plasticity During Facial Anethesia," Department of Health and Human Services, Public health Service, Grant No. 2 R01 DE11451-07, Apr. 2000.

Nicolelis, Miguel A.L., "Corticofugal Modulation of Tactile Sensory Processing," Department of Health and Human Services, Public Health Service, National Institute of Dental and Craniofacial Research of the Nationsl Institutes of health, Grant No. 1 R01 DE013810-01 A1, Jun. 2000.

Jonathan R. Wolpaw et al., "Brain-Computer Interface Technology: A Review of the First International Meeting," IEEE Transactions on Rehabilitation Engineering, vol. 8, No. 2, Jun. 2000, pp. 164-173.

Simon P. Levine et al., "A Direct Brain Interface Based on Event-Related potentials," IEEE Transactions on Rehabilitation Engineering, vol. 8, No. 2, Jun. 2000, pp. 180-185.

Robert E. Isaacs et al., "Work Toward Real-Time Control of a cortical Neural Prothesis," IEEE Transactions on Rehabilitation Engineering, vol. 8, No. 2, Jun. 2000, pp. 196-198.

Scott Makeig et al., A Natural Basis for Efficient Brain-Actuated Control, IEEE Transactions on Rehabilitation Engineering, vol. 8, No. 2, Jun. 2000, pp. 208-211.

Johan Wessberg et al., "Real-time prediction of hand trajectory by ensembles of cortical neurons in primates," Nature, vol. 408, Nov. 16, 2000, pp. 361-365.

Jerome N. Sanes et al., "Plasticity and Primary Motor Cortex," Annual Reviews, Neuroscience, Brown University, Library, vol. 23, 2000, pp. 393-415.

Jonathan C. Jarvis et al., "The application and technology of implantable neuromuscular stimulators: an introduction and overview," Medical Engineering & Physics, No. 23, Jan. 11, 2001, pp. 3-7.

Miguel A. L. Nicolelis, "Real-time direct interfaces between the brain and electronic and mechanical devices could one day be used to restore sensory and motor functions lost through injury or disease. Hybrid brain-machine interfaces also have the potential to enhance our perceptual, motor and cognitive capabilities by revolutionizing the way we use computers and interact with remote environments," Nature, vol. 409, Jan. 18, 2001, pp. 403-407.

Gerald E. Loeb et al., "BION™ system for distributed neural prosthetic interfaces," Medical Engineering & Physics, vol. 23, Jan. 26, 2001, pp. 9-18.

Patrick J. Rousche et al., "Flexible Polyimide-Based Intracortical Electrode Arrays with Bioactive Capability," IEEE Transactions on Biomedical Engineering, vol. 48, No. 3, Mar. 2001, pp. 361-371.

Nicolelis, Miguel A.L., "Trigeminal System Plasticity During Facial Anethesia," Department of Health and Human Services, Public Health Service, Grant No. 2 R01 DE11451-08, Apr. 2001.

Qing Bai et al., "Single-Unit Neural Recording with Active Microelectrode Arrays," IEEE Transactions on Biomedical Engineering, vol. 48, No. 8, Aug. 2001, pp. 911-920.

David L. Zealear et al., "The Biocompatibility, Integrity, and Positional Stability of an Injectable Microstimulator for Reanimation of the Paralyzed Larynx," IEEE Transactions on Biomedical Engineering, vol. 48, No. 8, Aug. 2001, pp. 890-897.

Dawn M. Taylor et al., "Using Virtual Reality to Test the Feasibility of Controlling an Upper Limb Fes System Directly from Multiunit Activity in the Motor Cortex," Arizona State University; and The Neurosciences Institute, Summer 2001, pp. 1-3.

Ranu Jung et al., "Real-Time Interaction Between a Neuromorphic Electronic Circuit and the Spinal Cord," IEEE Transactions on Neural Systems and Rehabilitation Engineering, vol. 9, No. 3, Sep. 2001, pp. 319-326.

Shay Shoham, "Advances Towards an Implantable Motor Cortical Interface," The University of Utah, Dec. 2001, pp. 1-157.

John K. Chapin et al., "Neural Prostheses for Restoration of Sensory and Motor Function," CRC Press, LLC, 2001, Chapters 6, 8 and 9 pp. 179-219, pp. 235-261, pp. 263-283.

Andrew B. Schwartz et al., "Extraction algorithms for cortical control of arm prosthetics," The Neuroscience Institute; and Department of Bioengineering, Arizona State University, 2001, pp. 701-707.

István Ulbert et al., "Multiple microelectrode-recording system for human intracortical applications," Journal of Neuroscience Methods, vol. 106, 2001, pp. 69-79.

Mijail D. Serruya et al., "Instant Neural Control of a Movement Signal," Nature, vol. 416, Mar. 14, 2002, pp. 141-142.

Nicolelis, Miguel A.L., "Corticofugal Modulation of Tactile Sensory Processing," Department of Health and Human Services, Public health Service, National Institute of Dental and Craniofacial Research of the Nationsl Institutes of Health, Grant No. 5 R01 DE013810-02, Mar. 2002.

Nicolelis, Miguel A.L., "Trigeminal System Plasticity During Facial Anethesia," Department of Health and Human Services, Public Health Service, Grant No. 2 R01 DE11451-09, Apr. 2002.

Dawn M. Taylor et al., "Direct Cortical Control of 3D Neuroprosthetic Devices," Science, vol. 296, Jun. 7, 2002, pp. 1829-1832.

John P. Donoghue, "Connecting cortex to machines: recent advances in brain interfaces," Nature Neuroscience Supplement, vol. 5, Nov. 2002, pp. 1085-1088.

Y. Gao, et al., "Probabilistic Inference of Hand Motion from Neural Activity in Motor Cortex," In Advances in Neural Information Processing Systems 14, The MIT Press, 2002, pp. 1-8.

Mijail Serruya et al., "Robustness of neuroprosthetic decoding algorithms," Biological Cybernetics, 2003, pp. 1-10.

Frank Wood et al., "On the Variability of Manual Spike Sorting," Brown University, Providence, RI, Jul. 1, 2003, pp. 1-19.

Wei Wu et al., "Modeling and Decoding Motor Cortical Activity using a Switching Kalman Filter,"Brown University, Providence, RI, Jul. 1, 2003, pp. 1-30.

Jose M. Carmena et al., "Learning to Control a Brain-Machine Interface for Reaching and Grasping by Primates," PLOS Biology, vol. 1, Issue 2, Oct. 13, 2003, pp. 1-16.

Nicolelis, Miguel A.L., "Brain-machine Interfaces to Restore Motor Function and Probe Neural Circuits," Nature Reviews, Neuroscience, vol. 4, May 2003, pp. 417-422.

Libet, Benjamin, "Unconscious Cerebral Initiative and the Role of Conscious Will in Voluntary Action," The Behavioral and Brain Sciences 1995) 8, pp. 529-566.

Norretranders, Tor, "The User Illusion," Penguin Books, 1991, Chapter 12, pp. 310-328.

Mohammad Mojarradi, "A Miniaturized Neuroprosthesis Suitable for Implantation Into the Brain," IEEE Transactions on Neural Systems and Rehabilitation Engineering, vol. 11, No. 1, Mar. 2003.

Morten K. Haugland et al., "Cutaneous Whole Nerve Recordings Used for Correction of Footdrop in Hemiplegic Man," IEEE Transactions on Neural Systems and Rehabilitation Engineering, vol. 3, No. 4, Dec. 1995.

Ferdinando Mussa-Ivaldi et al., "Brain-machine interfaces: computational demands and clinical needs meet basic neuroscience," TRENDS in Neurosciences, vol. 26, No. 6, Jun. 2003, pp. 329-334.

D.N. Harvey et al., "Multiple-Output Electromyographic Switching System," 1978 ISA, Pittsburgh, PA, 1978, pp. 121-123.

Faisal Karmali et al., "Environmental Control by a Brain-Computer Interface," Proceedings of the 22nd Annual EMBS Int'l Conf., Jul. 23-28, 2000, Chicago, IL, pp. 2990-2992.

Alex Mihailidis et al., "Using artificial intelligence to assist people with dementia to be more independent," Proceedings of the 22nd Annual EMBS Int'l Conf., Jul. 23-28, 2000, Chicago, IL, pp. 2993-2996.

Touradj Ebrahimi et al., "Brain-Computer Interface in Multimedia Communication," IEEE Signal Processing Magazine, vol. 20, No. 1, Jan. 2003, pp. 14-24.

Gernot R. Müller et al., "Implementation of a Telemonitoring System for the Control of an EEG-Based-Brain-Computer Interface," IEEE Transactions on Neural Systems and Rehabilitation Engineering, vol. 11, No. 1, Mar. 2002, pp. 54-59.

United States Patent and Trademark Office, Notification of First Office Action for U.S. Appl. No. 11/315,226, Mail Date Oct. 28, 2009.

United States Patent and Trademark Office, Notification of First Office Action for U.S. Appl. No. 11/315,254, Mail Date Nov. 2, 2009.

* cited by examiner

PATIENT TRAINING ROUTINE FOR BIOLOGICAL INTERFACE SYSTEM

This application claims the benefit of priority under 35 U.S.C. §119(e) of U.S. provisional application No. 60/642,021, filed Jan. 6, 2005. This application relates to commonly assigned U.S. application Ser. Nos. 11/315,254 and 11/315,226 of J. Christopher Flaherty et al., entitled "PATIENT TRAINING ROUTINE FOR BIOLOGICAL INTERFACE SYSTEM" and "ADAPTIVE PATIENT TRAINING ROUTINE FOR BIOLOGICAL INTERFACE SYSTEM," respectively, all of which are filed on the same date as the present application. The complete subject matter of each of the above-referenced applications is incorporated by reference herein.

FIELD OF THE INVENTION

The present invention relates to medical devices and, more particularly, biological interface systems that may include one or more devices controllable by processed multicellular signals of a patient. A processing unit produces a control signal based on multicellular signals received from a sensor comprising multiple electrodes. More particularly, the system includes a patient training routine that configures the system to optimize control of the device.

DESCRIPTION OF RELATED ART

Biological interface devices, for example neural interface devices, are currently under development for numerous patient applications including restoration of lost function due to traumatic injury or neurological disease. Sensors, such as electrode arrays, implanted in the higher brain regions that control voluntary movement, can be activated voluntarily to generate electrical signals that can be processed by a biological interface device to create a thought invoked control signal. Such control signals can be used to control numerous devices including computers and communication devices, external prostheses, such as an artificial arm or functional electrical stimulation of paralyzed muscles, as well as robots and other remote control devices. Patient's afflicted with amyotrophic lateral sclerosis (Lou Gehrig's Disease), particularly those in advanced stages of the disease, would also be appropriate for receiving a neural interface device, even if just to improve communication to the external world, including Internet access, and thus improve their quality of life.

Early attempts to utilize signals directly from neurons to control an external prosthesis encountered a number of technical difficulties. The ability to identify and obtain stable electrical signals of adequate amplitude was a major issue. Another problem that has been encountered is caused by the changes that occur to the neural signals that occur over time, resulting in a degradation of system performance. Neural interface systems that utilize other neural information, such as electrocorticogram (ECoG) signals, local field potentials (LFPs) and electroencephalogram (EEG) signals have similar issues to those associated with individual neuron signals. Since all of these signals result from the activation of large groups of neurons, the specificity and resolution of the control signal that can be obtained is limited. However, if these lower resolution signals could be properly identified and the system adapt to their changes over time, simple control signals could be generated to control rudimentary devices or work in conjunction with the higher power control signals processed directly from individual neurons.

Commercialization of these neural interfaces has been extremely limited, with the majority of advances made by universities in a preclinical research setting. As the technologies advance and mature, the natural progression will be to more sophisticated human applications, such as those types of devices regulated by various governmental regulatory agencies including the Food and Drug Administration in the United States.

As sophisticated biological interface systems are approved by the FDA and become commercially available, these systems need to include numerous safety features required for medical devices. It will also be required that the systems have simplified configuration routines, such as patient training routines, which assure reliable functionality. Convenience and flexibility to the patient, their caregivers and family members will also be a requirement. There is therefore a need for an improved biological interface system which includes a sophisticated patient training routine. Automation, as well as convenience to health care providers will provide numerous benefits to the patient and the health care system.

SUMMARY OF THE INVENTION

According to one exemplary aspect of the present disclosure, a biological interface system is disclosed. The biological interface system collects multicellular signals emanating from one or more living cells of a patient and transmits processed signals to a controlled device. For example, the system may include a sensor comprising a plurality of electrodes for detecting multicellular signals emanating from one or more living cells of a patient, and a processing unit configured to receive the multicellular signals from the sensor and process the multicellular signals to produce processed signals. The processing unit is also configured to transmit the processed signals to a controlled device that is configured to receive the processed signals. The processing unit is configured to perform an integrated patient training routine (such as an integrated software module) to generate one or more system configuration parameters that are used by the processing unit to produce the processed signals. The processing unit allows an operator to perform the integrated patient training routine at least one time during use of the system. For example, the system has an internal function that requires that an operator perform the integrated patient training routine at least one time during the use of the system.

According to another exemplary aspect of the invention, a biological interface system is disclosed. The biological interface system collects multicellular signals emanating from one or more living cells of a patient and transmits processed signals to a controlled device. The system includes a sensor for detecting multicellular signals, the sensor comprising a plurality of electrodes. The electrodes are designed to detect the multicellular signals. A processing unit is designed to receive the multicellular signals from the sensor and process the multicellular signals to produce the processed signals transmitted to the controlled device. The system further comprises an integrated patient training routine that provides a time varying stimulus to the patient, such as a moving object on a display screen, a moving mechanical object such as a moving wheelchair or moving robotic arm, and/or a device that actually moves one or more of the patients limbs. While the patient training routine is providing a first set of states of the time varying stimulus, the patient imagines a movement represented by the stimulus and the processing unit simultaneously stores a first set of multicellular signals received by the processing unit from the sensor.

The processing unit utilizes this first set of multicellular data to produce one or more system configuration parameters, including parameters that define a transfer function that can allow the processing unit to produce processed signals or a representation of the processed signals used in a subsequent training event as an additional form of feedback to the patient. The training patient training routine then provides a second set of states of the time varying stimulus, as well as a representation of the processed signals, utilizing similar feedback forms such as two moving objects on a visual display, or different feedback forms such as an audio signal for the time varying stimulus and a moving prosthetic leg for the representation of the processed signal. While the patient training routine provides a second set of states of the time varying stimulus as well as the representation of the processed signal, the patient imagines a movement represented by the stimulus and visualizes the representation of the processed signals based on that imagined movement, and the processing unit simultaneously stores a second set of multicellular signals received from the sensor.

According to still another exemplary aspect, a biological interface system is disclosed. The biological interface system collects multicellular signals emanating from one or more living cells of a patient and transmits processed signals to a controlled device. The system includes a sensor for detecting multicellular signals, the sensor comprising a plurality of electrodes. The electrodes are designed to detect the multicellular signals. A processing unit is designed to receive the multicellular signals from the sensor and process the multicellular signals to produce the processed signals transmitted to the controlled device. The system further comprises an integrated patient training routine that provides a time varying stimulus to the patient, such as a moving object on a display screen, a moving mechanical object such as a moving wheelchair or moving robotic arm, and/or a device that actually moves one or more of the patients limbs. While the patient training routine is providing a set of states of the time varying stimulus, the patient imagines a movement represented by the stimulus and the processing unit simultaneously stores a first set of multicellular signals received by the processing unit from the sensor.

The processing unit utilizes this set of multicellular data to produce one or more system configuration parameters, including parameters that define a transfer function that can allow the processing unit to produce processed signals or a representation of the processed signals used in a subsequent training event as an additional form of feedback to the patient. The set of states of the time varying stimulus are selected from a domain of values. Additional steps of providing a time varying stimulus and recording multicellular signal data, such as when additional feedback is provided in the form of a representation of the processed signal. The data collected is used to produce a final transfer function to produce the processed signals used to allow patient control of the controlled device. An allowable range of values of the processed signals exists within a subset of the time varying stimulus domain of values. The reduction of the allowable range, such as control of a cursor on a computer screen in which the patient training routine uses a higher resolution screen than the controlled device resolution, is performed to improve the performance, reliability, and potentially safety of control of the controlled device.

According to yet still another exemplary aspect, a biological interface system is disclosed. The biological interface system collects multicellular signals emanating from one or more living cells of a patient and transmits processed signals to a controlled device. The system includes a sensor for detecting multicellular signals, the sensor comprising a plurality of electrodes. The electrodes are designed to detect the multicellular signals. A processing unit is designed to receive the multicellular signals from the sensor and process the multicellular signals to produce the processed signals transmitted to the controlled device. The system further comprises an integrated patient training routine that is performed to generate one or more system configuration parameters or values, these parameters used by the processing unit to produce the processed signals. The patient training routine adapts, during its use, such as within a single patient training event, or between two patient training events. The routine adapts due to one or more factors such as a change in controlled device control performance, a change in multicellular signals or a change in a patient physiologic parameter such as a level of patient consciousness during a patient training event.

According to some exemplary aspects, a biological interface system is disclosed. The biological interface system collects multicellular signals emanating from one or more living cells of a patient and transmits processed signals to a controlled device. The system includes a sensor for detecting multicellular signals, the sensor comprising a plurality of electrodes. The electrodes are designed to detect the multicellular signals. A processing unit is designed to receive the multicellular signals from the sensor and process the multicellular signals to produce the processed signals transmitted to the controlled device. The system further comprises an integrated patient training routine that provides a time varying stimulus to the patient, such as a moving object on a display screen, a moving mechanical object such as a moving wheelchair or moving robotic arm, and/or a device that actually moves one or more of the patients limbs. While the patient training routine is providing a set of states of the time varying stimulus, the patient imagines a movement represented by the stimulus and the processing unit simultaneously stores a first set of multicellular signals received by the processing unit from the sensor. An operator can adjust the time varying stimulus provided to the patient. In an exemplary embodiment, the operator is the patient, and the patient adjusts the time varying stimulus for one or more reasons such as avoiding an imagined event that causes phantom pain or choosing an icon that better fits the imagined movement.

According to another aspect, a biological interface system is disclosed. The biological interface system collects multicellular signals emanating from one or more living cells of a patient and transmits processed signals to two controlled devices. The system includes a sensor for detecting multicellular signals, the sensor comprising a plurality of electrodes. The electrodes are designed to detect the multicellular signals. A processing unit is designed to receive the multicellular signals from the sensor and process the multicellular signals to produce the processed signals transmitted to the two controlled devices. The system further comprises an integrated patient training routine that provides a first time varying stimulus to the patient and a second time varying stimulus to the patient. While the patient training routine is providing a set of states of the first time varying stimulus, the patient imagines a movement represented by the stimulus and the processing unit simultaneously stores a first set of multicellular signals received by the processing unit from the sensor. The first set of multicellular signals is used to produce a transfer function used by the processing unit to produce the processed signals transmitted to the first controlled device. While the patient training routine is providing a set of states of the second time varying stimulus, the patient imagines a movement represented by the stimulus and the processing unit simultaneously stores a second set of multicellular signals received by the processing unit from the sensor. The second set of multicellular signals is used to produce a transfer function used by the processing unit to produce the processed signals transmitted to the second controlled device.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings.

DESCRIPTION OF THE EMBODIMENTS

Figure 1:
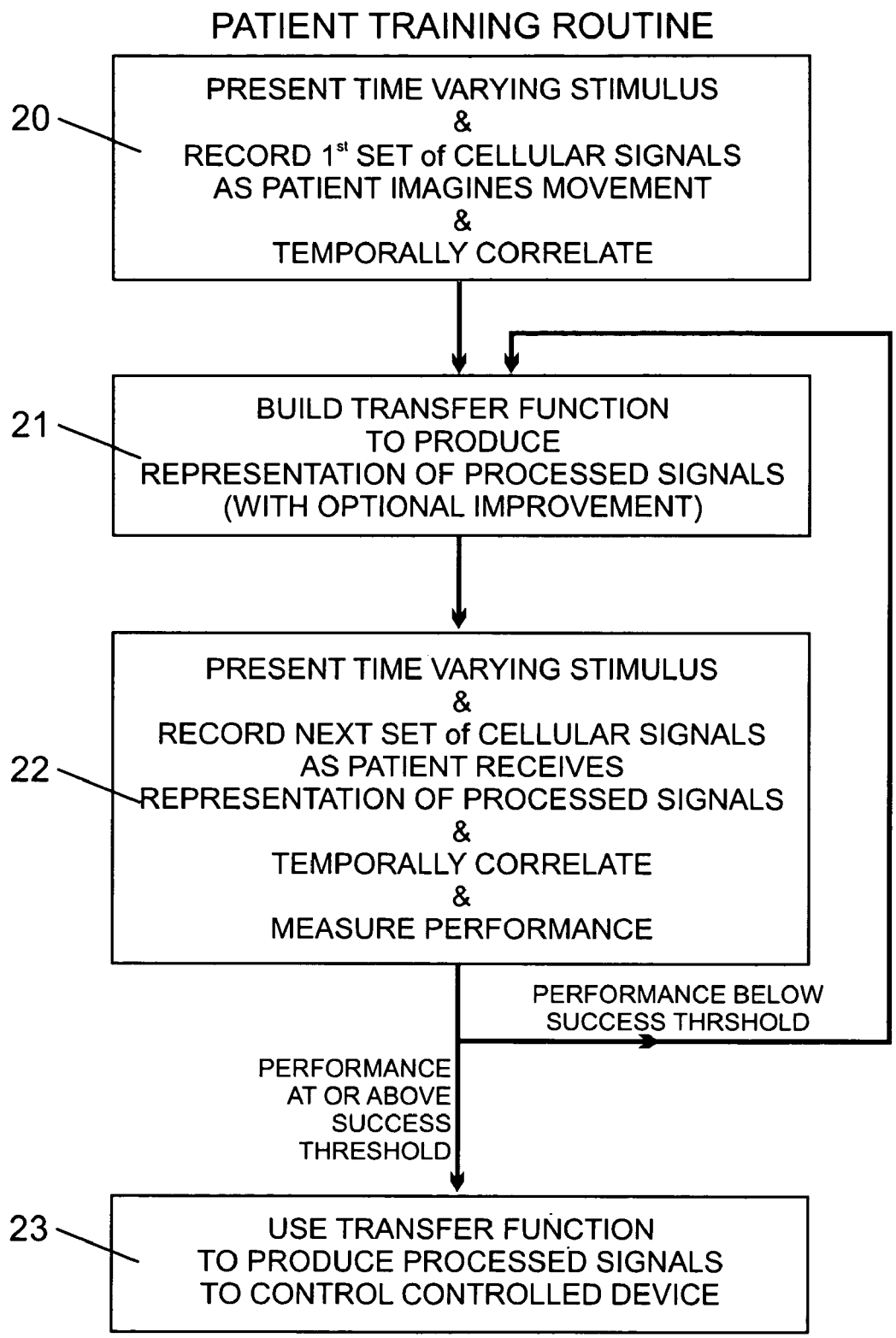
FIG. 1 illustrates a patient training routine flow chart of an exemplary embodiment of a biological interface system consistent with the present invention.

To facilitate an understanding of the invention, a number of terms are defined immediately herebelow.

Definitions

As used herein, the term "biological interface system" refers to a neural interface system or any system that interfaces with living cells that produce electrical activity or cells that produce other types of detectable signals.

The term "cellular signals," as used herein, refers to signals or combination of signals that may emanate from any living cell, such as, for example, subcellular signals, intracellular signals, and extracellular signals. For example, "cellular signals" may include, but not be limited to: neural signals (e.g., neuron action potentials or spikes, local field potential (LFP) signals, electroencephalogram (EEG) signals, electrocorticogram signals (ECoG), and signals whose frequency range falls between single neuron spikes and EEG signals); cardiac signals (e.g., cardiac action potentials); electromyogram (EMG) signals; glial cell signals; stomach cell signals; kidney cell signals; liver cell signals; pancreas cell signals; osteocyte cell signals; sensory organ cell signals (e.g., signals emanating from the eye or inner ear); tumor cell signals; and tooth cell signals.

The term "multicellular signals," as used herein, refers to signals emanating from two or more cells, or multiple signals emanating from a single cell. The term "subcellular signals," as used herein, refers to, for example, a signal derived from a part of a cell, a signal derived from one particular physical location along or within a cell, a signal from a cell extension (e.g., dendrite, dendrite branch, dendrite tree, axon, axon tree, axon branch, pseudopod, or growth cone), and signals from organelles (e.g., golgi apparatus or endoplasmic reticulum). The term "intracellular signals," as used herein, refers to a signal that is generated within a cell or by the entire cell that is confined to the inside of the cell up to and including the membrane. The term "extracellular signals," as used herein, refers to signals generated by one or more cells that occur outside of the cell(s).

As used herein, the term "patient" refers to any animal, such as a mammal and preferably a human. Specific examples of a "patient" include, but are not limited to: individuals requiring medical assistance; healthy individuals; individuals with limited function; and individuals with lost motor or other function due to traumatic injury or neurological disease.

As used herein, the term "configuration" refers to any alteration, improvement, repair, calibration, or other system modifying event whether manual in nature or partially or fully automated. The term "configuration parameter," as used herein, refers to a variable, or a value of the variable, of a component, device, apparatus, and/or system. A configuration parameter has a value that can be: set or modified; used to perform a function; used in a mathematical or other algorithm; used as a threshold to perform a comparison; and any combinations thereof. A configuration parameter's value determines the characteristics or behavior of something. System configuration parameters are variables of the system of the present invention, such as those used to by the processing unit to produce processed signals. Other, numerous subsets of configuration parameters are applicable, these subsets including but not limited to: calibration parameters such as a calibration frequency parameter; controlled device parameters such as a time constant parameter; processing unit parameters such as a cell selection criteria parameter; patient parameters such as a patient physiologic parameter such as heart rate; multicellular signal sensor parameters; other sensor parameters; system environment parameters; mathematical algorithm parameters; a safety parameter; and other parameters. Certain parameters may be controlled by the patient's clinician, such as a password-controlled parameter securely controlled by an integral permission routine of the system. Certain parameters may represent a "threshold" such as a success threshold used in a comparison to determine if the outcome of an event was successful. In numerous steps of a system configuration or other function, a minimum performance or other measure may be maintained by comparing a detected signal, or the output of an analysis of one or more signals, to a success threshold.

As used herein, the term "discrete component" refers to a component of a system such as those defined by a housing or other enclosed or partially enclosed structure, or those defined as being detached or detachable from another discrete component. Each discrete component can transmit information to a separate component through the use of a physical cable, including one or more of electrically conductive wires or optical fibers, or transmission of information can be accomplished wirelessly. Wireless communication can be accomplished with a transceiver that may transmit and receive data such as through the use of "Bluetooth" technology or according to any other type of wireless communication means, method, protocol or standard, including, for example, code division multiple access (CDMA), wireless application protocol (WAP), Infrared or other optical telemetry, radio frequency or other electromagnetic telemetry, ultrasonic telemetry or other telemetric technologies.

As used herein, the term "routine" refers to an established function, operation, or procedure of a system, such as an embedded software module that is performed or is available to be performed by the system. Routines may be activated manually such as by an operator of a system, or occur automatically such as a routine whose initiation is triggered by another function, an elapsed time or time of day, or other trigger. The devices, apparatus, systems and methods of the present invention may include or otherwise have integrated into one or their components, numerous types and forms of routines. An "adaptive processing routine" is activated to determine and/or cause a routine or other function to be modified or otherwise adapt to maintain or improve performance. A competitive routine is activated to provide a competitive function for the patient of the present invention to compete with, such as a function which allows an operator of the system to compete with the patient in a patient training task; or an automated system function which controls a visual object which competes with a patient controlled object. A "configuration routine" is activated to configure one or more system configuration parameters of the system, such as a parameter that needs an initial value assigned or a parameter that needs an existing parameter modified. A "language selection routine" is activated to change a language displayed in text form on a display and/or in audible form from a speaker. A "patient training routine" is activated to train the patient in the use of the system and/or train the system in the specifics of the patient, such as the specifics of the patient's multicellular signals that can be generated by the patient and detected by the sensor. A "permission routine" is activated when a system configuration or other parameter is to be initially set or modified in a secured manner. The permission routine may use one or more of: a password; a restricted user logon function; a user ID; an electronic key; a electromechanical key; a mechanical key; a specific Internet IP address; and other means of confirming the identify of one or more operators prior to allowing a secure operation to occur. A "remote technician routine" is activated to allow an operator to access the system of the present invention, or an associated device, from a location remote from the patient, or a system component to be modified. A "system configuration routine" is activated to configure the system, or one or more components or associated devices of the system. In a system configuration routine, one or more system configuration parameters may be modified or initially set to a value. A "system reset routine" is activated to reset the entire system or a system function. Resetting the system is sometimes required with computers and computer based devices such as during a power failure or a system malfunction.

General Description of the Embodiments

Systems, methods, and devices consistent with the invention detect cellular signals generated within a patient's body and implement various signal processing techniques to generate processed signals for transmission to one or more devices to be controlled. The system includes a sensor comprising a plurality of electrodes that detect multicellular signals from one or more living cells, such as from the central or peripheral nervous system of a patient. The system further includes a processing unit that receives and processes the multicellular signals and transmits a processed signal to a controlled device. The processing unit utilizes various electronic, mathematic, neural net, and other signal processing techniques in producing the processed signal.

An integrated patient training routine is embedded in one or more components of the system. The patient training routine may be a requirement of the system prior to allowing full control of the controlled device to the patient. The patient training routine can be utilized to develop a transfer function to apply to the multicellular signals to produce the processed signal. The patient training routine may involve a controlled device surrogate, such as a surrogate which has more complex functionality or control required than the intended control device. The patient training routine may adapt over time, such as to improve system performance and/or reduce the patient requirements of the routine. The patient training routine includes one or more time varying stimulus and, in some exemplary embodiments, the form, configuration, or type of the time varying stimulus is adjustable such as by the patient. In an alternative configuration, multiple controlled devices are included in the system and multiple training routines correspond to the multiple controlled devices.

Detailed Description of the Embodiments

Reference will now be made in detail to the present embodiments of the invention, examples of which are illustrated in the accompanying drawings. Wherever possible, the same reference numbers will be used throughout the drawings to refer to the same or like parts.

Referring now to FIG. 1, a flow chart of the patient training routine of the present invention is illustrated. The flow chart shows multiple steps and conditional statements that determine the progression from step to step. The patient training routine is preferably a software program, embedded in one or more components of the system such as the processing unit. Alternatively, an additional component is included in the system, such as a computer system to configure the system, and the patient training routine is embedded in whole or in part in the additional component. The patient training routine may be activated automatically by the system, or an operator of the system, such as the patient's clinician or the patient themselves, may initiate and/or conduct the patient training routine.

Referring back to FIG. 1, Step 20 includes the patient training routine providing to the patient a set of states of a time varying stimulus. The time varying stimulus can provide a target for a patient's imagined movement and/or simply be a trigger to initiate the imagined movement. The time varying stimulus can be provided in multiple forms such as: visual; tactile; auditory; olfactory; gustatory; electrical stimulation such as cortical stimulation; and any combinations thereof. The time varying stimulus may be provided in many different types such as: computer icon; visual display object; moveable mechanical assembly such as a robotic arm; vehicle such as a wheelchair; single or multi-frequency sound; stimulation electrode such as cortical stimulation electrode; robot or robotic component; tactile transducer such as vibrating skin patch; and any combinations thereof. The time varying stimulus can include continuous or semi-continuous motion such as an icon moving on a computer screen. The time varying stimulus can include a mechanical object moving in space, such as a robotic arm or a prosthetic limb. The time varying stimulus can be provided via one or more controlled devices of the system, such as an exoskeleton device or FES device moving one of the patient's own limbs. The time varying stimulus may be provided as a short duration stimulus, such as an object that appears on a visual display for less than one second, or a brief flash of light.

In a preferred embodiment, the time varying stimulus has an adjustable parameter, such as a parameter adjustable in a secured manner such as via the permission routine described hereabove. One or more parameters of the time varying stimulus may have a range of applicable values, such as a range of position of a cursor or icon on a computer screen, and these types of ranges may be an adjustable parameter. Other adjustable parameters include but are not limited to: display brightness or contrast; display size; display resolution; electrical current parameter such as current or voltage; object velocity, acceleration and position; object size and color; sound volume; sound frequency; tactile sensor force, frequency and pulse width; and any combinations thereof. The adjustment to a time varying stimulus parameter may be accomplished by one or more components of the system, such as the processing unit. The adjustment may be accomplished by one or more users of the system, such as the patient utilizing an input device selected from the group consisting of: chin joystick; eyebrow EMG switch; EEG activated switch such as the switched manufactured by BrainFingers of Yellow Springs, Ohio, USA; eye tracker such as the device manufactured by LC Technologies of Fairfax, Va., USA; a head tracker such as the device manufactured by Synapse Adaptive of San Rafael, Calif., USA; neck movement switch; shoulder movement switch; sip-n-puff joystick controller such as the controller manufactured by QuadJoy of Sheboygan, Wis., USA; speech recognition switch; tongue switch such as a tongue palate switch; and any combinations thereof.

Referring back to FIG. 1, Step 20 further includes the step of recording and storing, such as in electronic memory of a system component such as the processing unit, a first set of multicellular signals simultaneous with the patient imagining a movement associated with the provided set of states of the time varying stimulus. In a preferred embodiment, in a previous step, not shown, the patient has viewed the set of states of the time varying stimulus at least one time prior to the recording of the first set of multicellular signals. The first set of cellular signals are correlated, or mapped, to the set of states of the time varying stimulus. The correlation can be synchronized in time, called temporal mapping, or correlated to another parameter including but not limited to: a patient physiologic parameter such as heart rate; a controlled device parameter; a system environment parameter; a password controlled parameter; a clinician controlled parameter; a patient training routine parameter; and any combinations thereof.

Step 21 includes the building of a transfer function that is used to build a representation of the processed signals. The representation of the processed signal is a precursor to the processed signals used to control the controlled device. The representation of the processed signals may temporarily control the controlled device, a surrogate of the controlled device, or another device. In order to produce the processed signals, the processing unit includes a transfer function that is applied to the multicellular signals. The transfer function includes and/or is based upon one or more system configuration parameters that are generated and/or modified by the patient training routine. The representation of the processed signal is also produced with a transfer function that is applied to the multicellular signals, such as a transfer function that has parameters determined based on the temporal correlation of the first set of multicellular signals and the first set of states of the time varying stimulus. In an alternative, preferred embodiment, the representation of processed signals is modified with a bias toward a time varying stimulus that acts as a target for the patient's imagined movement. This improved control signal can be used as a motivator to the patient, and preferably has its improvement bias decrease as patient control performance increases.

Step 22 includes the patient training routine providing a set of states of a time varying stimulus and the representation of the processed signal whose transfer function is created in Step 21. While the patient receives, such as through viewing a visual display, listening to an audio signal, and/or feeling a tactile transducer, both the set of states of the time varying stimulus as well as the patient controlled feedback produced by the representation of processed signals, a next set of multicellular signals are recorded and stored. This next set is also correlated to the set of states of the time varying stimulus, such as a temporal correlation and/or other correlation described hereabove. The representation of the processed signal and/or the time varying stimulus can be presented via the controlled device, a controlled device surrogate, or another device. The controlled device surrogate can be configured to be more complex than the intended controlled device, such that the patient is training with a more complicated device to improve eventual controlled device control. The surrogate device may have one or more differences, such as a larger value of one or more of: degrees of freedom; resolution; modes; discrete states; functions; boundary conditions; and any combinations thereof. The boundary conditions of the surrogate can differ in one or more of: maximum distance; maximum velocity; maximum acceleration; maximum force; maximum torque; rotation; position; and any combinations thereof.

The representation of the processed signals may be provided in a form similar to the time varying stimulus, or in a different form. In a preferred embodiment, the time varying stimulus is provided as an object on a visual display, and the representation of processed signals is the motion of a mechanical object such as a prosthetic limb. Both the time varying stimulus and the representation of processed signals can be provided in multiple forms selected from at least one of: visual; tactile; auditory; olfactory; gustatory; and electrical stimulation such as cortical stimulation. Both the time varying stimulus and/or the representation of processed signals can be provided as one or more of: moving object on screen; moving mechanical device such as a mechanical limb or wheelchair; moving part of patient's body such as via an exoskeleton device or FES device; changing audible signal such as a multi-frequency signal; and any combinations thereof.

As shown in FIG. 1, step 22 also includes the measuring of the performance of the representation of the processed signal as compared to the time varying stimulus. In a preferred embodiment, both the time varying stimulus and the representation of processed signals are presented as an object on a computer screen, and the performance is based on the ability of the patient to track the time varying stimulus object with the patient controlled object controlled by the representation of the processed signals. A performance measure value is determined and this value is compared to a predetermined success threshold value. If the performance measure value is at or above the success threshold value, the next step to be followed is Step 23 in which the patient training routine is completed and the current transfer function is subsequently used produce the processed signals to control the controlled device. If the performance measure value is below the success threshold value, the next step to be followed is a repeat of step 21 and its subsequent steps. In a preferred embodiment, the success threshold value is a system configuration parameter that is adjustable such as via a remote operator in which the permission routine is invoked to complete the change.

As stated above, if the performance meets or exceeds the threshold, the patient training routine proceeds to Step 23 wherein the processing unit utilizes the transfer function determined in the patient training routine to convert the multicellular signals received from the sensor of the present invention, and produces the processed signals to be transmitted to the controlled devices. In a preferred embodiment, a third set of states of time varying stimulus and a second representation of processed signals are used to create the transfer function. The second representation of processed signals is based on a second set of multicellular signals previously recorded, or a combination of the first and second sets of multicellular signal data. In another preferred embodiment, the patient training routine must be performed at least one time in the use of the system, such as prior to the patient receiving full control of the controlled device. In an alternative embodiment, the patient training routine must be performed at least two times in the use of the system. In another preferred embodiment, the patient training routine must be successfully completed, such as when a performance parameter meets or exceeds a success threshold value, prior to the patient receiving full control of the controlled device. Full control of a controlled device is described in greater detail in reference to FIG. 3 herebelow.

In another preferred embodiment, the system of the present invention includes two controlled devices, and the patient training routine provides different feedback to the patient during the routine, such as different time varying stimulus or other feedback. Alternatively or additionally, the system may include a separate patient training routine for each controlled device. For the multiple controlled devices, a first set of states for a time varying stimulus will be provided to develop a transfer function for the first controlled device, and a second set of states for a time varying stimulus will be provided to develop a transfer function for the second controlled device. In a preferred embodiment, the first controlled device is a prosthetic or exoskeleton driven arm, and the second controlled device is a prosthetic or exoskeleton driven leg. In another preferred embodiment, the first controlled device is a prosthetic or exoskeleton driven arm, and the second controlled device is a vehicle such as a wheelchair.

As stated above, the patient training routine can be used to generate one or more system configuration parameters used by the processing unit to develop a transfer function to produce processed signals. The selection of cells for processing as well as criteria for selecting cells may be generated. A signal processing parameter can be generated such as a coefficient modifying one or more of the following: amplification, filtering, sorting, conditioning, translating, interpreting, encoding, decoding, combining, extracting, sampling, multiplexing, analog to digital converting, digital to analog converting, mathematically transforming; and any combinations thereof. A control signal transfer function parameter, such as a coefficient value; algorithm; methodology; mathematical equation; and any combinations of those may be generation. A calibration parameter such as calibration frequency and/or a controlled device parameter such as a controlled device parameter boundary limit may be generated. Other system configuration parameters that can be generated by the patient training routine include but are not limited to: acceptable frequency range of cellular activity; selection of electrodes to include; selection of cellular signals to include; type of frequency analysis such as power spectral density; instruction information to patient such as imagined movement type or other imagined movement instruction; type, mode or configuration of feedback during provision of processed signal to patient; calibration parameter such as calibration duration and calibration frequency; controlled device parameter such as controlled device mode; alarm or alert threshold; success threshold; and any combinations thereof.

In another preferred embodiment, the patient training routine of the present invention adapts over time. Each time the patient training routine is invoked, a patient training event, one or more changes may be made for the next patient training event. A change may be caused by a measurement of performance, such as controlled device control performance. A control at or above a threshold, measured as has been described in detail hereabove, may result in a subsequent patient training routine of a shorter duration. Alternatively, performance below a similar threshold may result in a longer patient training routine, and/or a modified patient training routine. The patient training routine may adapt based on a multicellular signal change, such as the death of one or more cells previously providing cellular signals. The patient training routine may adapt due to a change in a patient parameter, such as a change due to a change in patience consciousness level. In the circumstance wherein patience consciousness falls below a threshold, a patient training routine may adapt within the routine itself—such as to repeat a step, or delay a step until consciousness is at a higher level. Patient consciousness may be measured using the multicellular signals of the sensor of the present invention, or another sensor of the system such as an EEG or LFP sensor.

In another preferred embodiment, the patient training routine automatically adapts, such as by being triggered by a system-monitored parameter crossing a threshold. Alternatively, the routine may adapt based on an operator input. Routines may adapt within a single patient training event, or between patient training events. Routines may adapt based on a measure of performance in a previous patient training routine event, or based on a comparative difference between two patient training events.

Figure 2:
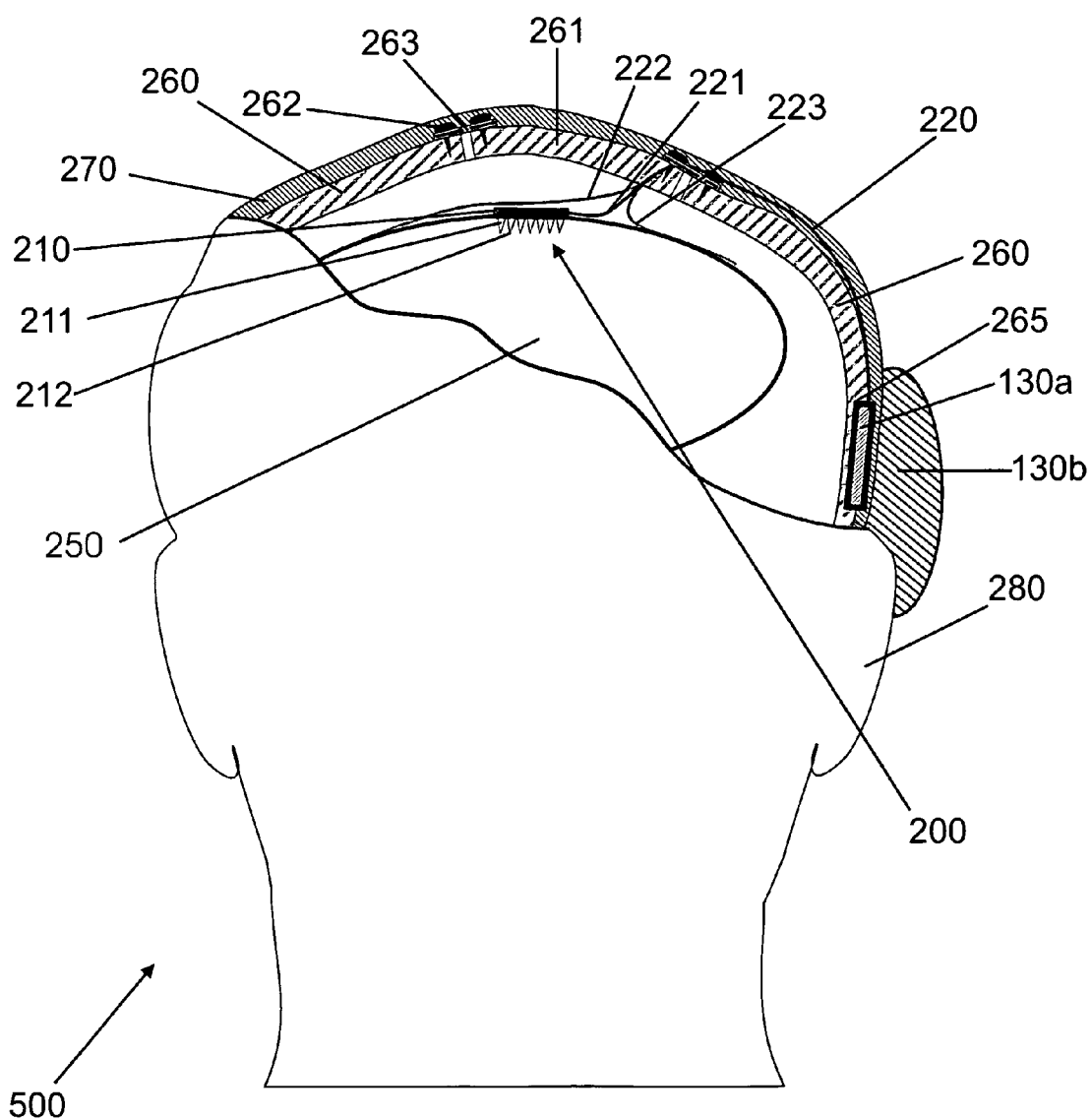
FIG. 2 illustrates an exemplary embodiment of a portion of the biological interface system consistent with the present invention wherein sensor electrodes are implanted in the brain of a patient and a portion of a processing unit is implanted on the skull of the patient.

Referring now to FIG. 2, a brain implant apparatus consistent with an embodiment of the present invention is illustrated. As shown in FIG. 2, the system includes an array of electrodes assembly (e.g., sensor 200), which has been inserted into a brain 250 of patient 500, through a previously created opening in scalp 270 and skull 260 in a surgical procedure known as a craniotomy. Sensor 200 includes a plurality of longitudinal projections 211 extending from a base (e.g., array substrate 210). Projections 211 may be rigid, semi-flexible or flexible, the flexibility such that each projection 211 can still penetrate into neural tissue, potentially with an assisting device or with projections that only temporarily exist in a rigid condition. Sensor 200 has been inserted into brain 250, preferably using a rapid insertion tool, such that the projections 211 pierce into brain 250 and sensor substrate 210 remains in close proximity to or in light contact with the surface of brain 250. At the end of each projection 211 is an electrode 212. In alternative embodiments, electrodes can be located at a location other than the tip of projections 211 or multiple electrodes may be included along the length of one or more of the projections 211. One or more projections 211 may be void of any electrode, such projections potentially including anchoring means such as bulbous tips or barbs.

Electrodes 212 are configured to detect electrical brain signals or impulses, such as individual neuron spikes or signals that represent clusters of neurons such as local field potential (LFP) and electroencephalogram (EEG) signals. Each electrode 212 may be used to individually detect the firing of multiple neurons, separated by neuron spike discrimination techniques. Other applicable signals include electrocorticogram (ECoG) signals and other signals, such as signals between single neuron spikes and EEG signals. Sensor 200 may be placed in any location of a patient's brain allowing for electrodes 212 to detect these brain signals or impulses. In a preferred embodiment, electrodes 212 can be inserted into a part of brain 250 such as the cerebral cortex. Alternative forms of penetrating electrodes, such as wire or wire bundle electrodes, can make up or be a component of the sensor of the present invention. In addition to or alternative from neural signals, the system of the present invention may utilize other types of cellular signals to produce a processed signal to control a device. The various forms of penetrating electrodes described above can be placed into tissue within or outside of the patient's cranium, such tissue including but not limited to: nerve tissue such as peripheral nerve tissue or nerves of the spine; organ tissue such as heart, pancreas, liver or kidney tissue; tumor tissue such as brain tumor or breast tumor tissue; other tissue and combinations thereof.

Alternatively or additionally, the sensor of the present invention may employ non-penetrating electrode configurations, not shown, such as subdural grids placed inside the cranium such as to record LFP signals. In addition to subdural grids, the sensor may comprise other forms of non-penetrating electrodes such as flat electrodes, coil electrodes, cuff electrodes and skin electrodes such as scalp electrodes. These non-penetrating electrode configurations are placed in, on, near or otherwise in proximity to the cells whose signals are to be detected, such as neural or other cellular signals. In another alternative embodiment, the sensor of the present invention includes detectors other than electrodes, such as photodetectors that detect cellular signals represented by a light emission. The light emission can be caused by a photodiode, integrated into the sensor or other implanted or non-implanted system component, shining one or more wavelengths of light on the appropriate cells. In addition to the numerous types of cells described above, one or more of the various configurations of the sensor of the present invention may utilize any living cell of the body that emanates cellular signals. In a preferred embodiment, the cellular signals are under voluntary control of the patient.

Although FIG. 2 depicts sensor 200 as a single discrete component, in alternative embodiments the sensor may comprise multiple discrete components, including one or more types of electrodes or other cellular signal detecting elements, each configured and placed to detect similar or dissimilar types of cellular signals. Multiple sensor discrete components can be implanted entirely within: the skull, an extracranial location such as a peripheral nerve, or external to the body; or the components can be placed in any combination of these locations.

Sensor 200 serves as the multicellular signal sensor of the biological interface system of the present invention. While FIG. 2 shows sensor 200 as eight projections 211 with eight electrodes 212, sensor 200 may include one or more projections with and without electrodes, both the projections and electrodes having a variety of sizes, lengths, shapes, surface areas, forms, and arrangements. Moreover, sensor 200 may be a linear array (e.g., a row of electrodes) or a two-dimensional array (e.g., a matrix of rows and columns of electrodes such as a ten by ten array), or wire or wire bundle electrodes. An individual wire lead may include a plurality of electrodes along its length. Projections and electrodes may have the same materials of construction and geometry, or there may be varied materials and/or geometries used in one or more electrodes. Each projection 211 and electrode 212 of FIG. 2 extends into brain 250 to detect one or more cellular signals such as those generated from the neurons located in proximity to each electrode 212's placement within the brain. Neurons may generate such signals when, for example, the brain instructs a particular limb to move in a particular way and/or the brain is planning that movement. In a preferred embodiment, the electrodes reside within the arm, hand, leg or foot portion of the motor cortex of the brain. The processing unit of the present invention may assign one or more specific cellular signals to a specific use, such as a specific use correlated to a patient imagined event. In a preferred embodiment, the one or more cellular signals assigned to a specific use are under voluntary control of the patient.

Referring back to FIG. 2, the processing unit of the present invention includes processing unit first portion 130a, placed under scalp 270 at a location near patient 500's ear 280. Processing unit first portion 130a receives cellular signals from sensor 200 via wire bundle 220 (e.g., a multi-conductor cable). In a preferred embodiment, wire bundle 220 includes a conductor for each electrode 212. Processed signals are produced by processing unit first portion 130a and other processing unit discrete components, such as processing unit second portion 130b removably placed on the external skin surface of patient 500 near ear 280. Processing unit second portion 130b remains in relative close proximity to implanted component processing unit first portion 130a through one or more fixation means such as cooperative magnetic means in both components, or body attachment means such that the processing unit second portion 130b is attached to eye glasses, an ear wrapping arm, a hat, mechanical straps, or an adhesive pad. Processing unit first portion 130a and processing unit second portion 130b work in combination to receive multicellular signal data and create a time code of brain activity.

In the preferred embodiment depicted in FIG. 2, bone flap 261 (e.g., the original bone portion removed in the craniotomy) may be used to close the hole made in the skull 260 during the craniotomy, obviating the need for a prosthetic closure implant. Bone flap 261 is attached to skull 260 with one or more straps (e.g., bands 263), which preferably comprises titanium or stainless steel. Band 263 is secured to bone flap 261 and skull 260 with bone screws 262. Wire bundle 220 passes between bone flap 261 and the hole cut into skull 260. During the surgical procedure, bone recess 265 was made in skull 260 such that processing unit first portion 130a could be placed in the indentation, allowing scalp 270 to lie relatively flat and free of tension in the area proximal to processing unit first portion 130a. A long incision in scalp 270 between the craniotomy site and the recess 265 can be made to place processing unit first portion 130a in recess 265. Alternatively, an incision can be made to perform the craniotomy, and a separate incision made to form recess 265, after which the processing unit first portion 130a and wire bundle 220 can be tunneled under scalp 270 to the desired location. Processing unit first portion 130a is attached to skull 260 with one or more bone screws or a biocompatible adhesive.

In an alternative embodiment, processing unit first portion 130a may be placed entirely within skull 260 or be geometrically configured and surgically placed to fill the craniotomy hole instead of bone flap 261. Processing unit first portion 130a can be placed in close proximity to sensor 200, or a distance of 5-20 cm can separate the two components. Processing unit first portion 130a includes a biocompatible housing which creates a fluid seal around wire bundle 220 and numerous internal components of processing unit first portion 130a, internal components not shown. Internal components of Processing unit first portion 130a may provide one or more of the following functions: signal processing of the cellular signals received from sensor 200 such as buffering, amplification, digital conversion and multiplexing, wireless transmission of cellular signals, a partially processed, or derivative form of the cellular signals, or other data; inductive power receiving and conversion; and other functions well known to implanted electronic assemblies such as implanted pacemakers, defibrillators, and pumps.

Processing unit second portion 130b, removably placed at a location proximate to implanted processing unit first portion 130a, but external to patient 500, receives data from processing unit first portion 130a via wireless communication through the skin, such as infrared or radiofrequency wireless data transfer means. Processing unit second portion 130b includes, in addition to wireless data receiving means, wireless power transfer means such as an RF coil which inductively couples to an implanted coil, signal processing circuitry, an embedded power supply such as a battery, and data transfer means. The data transfer means of processing unit second portion 130b may be wired or wireless, and transfer data to one or more of: implanted processing unit first portion 130a; a different implanted device; and an external device such as an additional component of the processing unit of the present invention, a controlled device of the present invention or a computer device such as a configuration computer with Internet access.

Referring back to FIG. 2, electrodes 212 transfer the detected cellular signals to processing unit first portion 130a via array wires 221 and wire bundle 220. Wire bundle 220 includes multiple conductive elements and array wires 221, which preferably include a conductor for each electrode 212 of sensor 200. Also included in wire bundle 220 are two conductors: first reference wire 222 and second reference wire 223, each of which is placed in an area in relative proximity to sensor 200 such as on the surface of brain 250 near the insertion location. First reference wire 222 and second reference wire 223 may be redundant and provide reference signals used by one or more signal processing elements of the processing unit of the present invention to process the cellular signal data detected by one or more electrodes. In an alternative embodiment, not shown, sensor 200 may comprise multiple discrete components and multiple bundles of wires connect to one or more discrete components of the processing unit, such as processing unit first portion 130a. In another alternative embodiment, cellular signals detected by sensor 200 are transmitted to processing unit first portion 130a via wireless technologies, such as infrared communication incorporated into an electronic module of sensor 200. Such transmissions penetrate the skull of the patient, obviating the need for wire bundle 220, array wires 221, and any physical conduit passing through skull 260 after the surgical implantation procedure is completed.

Processing unit first portion 130a and processing unit second portion 130b independently or in combination preprocess the received cellular signals (e.g., impedance matching, noise filtering, or amplifying), digitize them, and further process the cellular signals to extract neural data that processing unit second portion 130b may then transmit to an external device, such as an additional processing unit component and/or any device to be controlled by the processed multicellular signals. For example, the external device may decode the received neural data into control signals for controlling a prosthetic limb or limb assist device or for controlling a computer cursor. In an alternative embodiment, the external device may analyze the neural data for a variety of other purposes. In another alternative embodiment, the device receiving transmissions from processing unit second portion 130b is an implanted device. Processing unit first portion 130a and processing unit second portion 130b independently or in combination include signal processing circuitry to perform multiple signal processing functions including but not limited to: amplification, filtering, sorting, conditioning, translating, interpreting, encoding, decoding, combining, extracting, sampling, multiplexing, analog to digital converting, digital to analog converting, mathematically transforming and/or otherwise processing cellular signals to generate a control signal for transmission to a controlled device. Processing unit first portion 130a and processing unit second portion 130b may include one or more components to assist in processing the multicellular signals or to perform additional functions. These components include but are not limited to: a temperature sensor; a pressure sensor; a strain gauge; an accelerometer; a volume sensor; an electrode; an array of electrodes; an audio transducer; a mechanical vibrator; a drug delivery device; a magnetic field generator; a photo detector element; a camera or other visualization apparatus; a wireless communication element; a light producing element; an electrical stimulator; a physiologic sensor; a heating element; and a cooling element.

Processing unit first portion 130a transmits raw or processed cellular signal data to processing unit second portion 130b through integrated wireless communication means, such as the infrared communication means of FIG. 2, or alternative means including but not limited to radiofrequency communications, other optical communications, inductive communications, ultrasound communications and microwave communications. In a preferred, alternate embodiment, processing unit first portion 130a includes both infrared communication means for short-range high baud rate communication, and radiofrequency communication means for longer range, lower baud rate communication. This wireless transfer allows sensor 200 and processing unit first portion 130a to be completely implanted under the skin of the patient, avoiding the need for implanted devices that require protrusion of a portion of the device or wired connections through the skin surface. In an alternative embodiment, a through the skin pedestal connector is utilized between either the implanted sensor 200 or processing unit first portion 130a and an external component. Processing unit first portion 130a includes a coil, not shown, which receives power through inductive coupling, on a continual or intermittent basis from an external power transmitting device such as processing unit second portion 130b. The inductive coupling power transfer configuration obviates the need for any permanent power supply, such as a battery, integral to processing unit first portion 130a.

In addition to or in place of power transmission, the integrated coil of processing unit first portion 130a and its associated circuitry may receive data from an external coil whose signal is modulated in correlation to a specific data signal. The power and data can be delivered to processing unit first portion 130a simultaneously such as through simple modulation schemes in the power transfer that are decoded into data for processing unit first portion 130a to use, store or facilitate another function. A second data transfer means, in addition to a wireless means such as an infrared LED, can be accomplished by modulating a signal in the coil of processing unit first portion 130a that data is transmitted from the implant to an external device including a coil and decoding elements. In a preferred embodiment, the processing unit first portion 130a includes an embedded ID, which can be wirelessly transmitted to the processing unit second portion 130b or a separate discrete component via the various wireless transmission means described above. In another preferred embodiment, processing unit second portion 130b includes means of confirming proper ID from processing unit first portion 130a, and processing unit second portion 130b also includes an embedded ID.

Processing unit first portion 130a and processing unit second portion 130b may independently or in combination conduct adaptive processing of the received cellular signals by changing one or more parameters of the system to achieve acceptable or improved performance. Examples of adaptive processing include, but are not limited to: changing a system configuration parameter during a system configuration; changing a method of encoding neural or other cellular signal data; changing the type, subset, or amount of cellular signal data that is processed; or changing a method of decoding neural or other cellular signal data. Changing an encoding method may include changing neuron spike sorting methodology, calculations, thresholds, or pattern recognition methodologies. Changing a decoding methodology may include changing variables, coefficients, algorithms, and/or filter selections. Other examples of adaptive processing may include changing over time the type or combination of types of signals processed, such as EEG, ECoG, LFP, neural spikes, or other cellular signal types.

Processing unit first portion 130a and processing unit second portion 130b may independently or in combination also transmit electrical signals to one or more electrodes 212 such as to stimulate, polarize, hyperpolarize or otherwise cause an effect on one or more cells of neighboring tissue. Specific electrodes may record cellular signals only, or deliver energy only, and specific electrodes may provide both functions. In an alternative embodiment, a separate device, not shown but preferably an implanted device with the ability to independently or in combination provide an electrical signal to multiple electrodes, delivers stimulating energy to one or more electrodes 212 or different electrodes. Stimulating electrodes in various locations can transmit signals to the central nervous system, peripheral nervous system, other body systems, body organs, muscles and other tissue or cells. The transmission of these signals is used to perform one or more functions including but not limited to: pain therapy; muscle stimulation; seizure disruption; stroke rehabilitation; coma recovery; and patient feedback.

In an alternative embodiment, processing unit first portion 130a and potentially additional signal processing functions are integrated into sensor 200, such as, for example, through the use of a bonded electronic microchip. In another alternative embodiment, processing unit first portion 130a may also receive non-neural cellular signals and/or other biologic signals, such as from an implanted sensor. These signals may be in addition to received neural multicellular signals, and they may include but are not limited to: EKG signals, respiration signals, blood pressure signals, electromyographic activity signals and glucose level signals. Such biological signals may be used to change the state of the biological interface system of the present invention or one of its discrete components. Such state changes include but are not limited to: turn system or component on or off; to begin a configuration routine; to initiate or conclude a step of a configuration or other routine; and to start or stop another system function. In another alternative embodiment, processing unit first portion 130a and processing unit second portion 130b independently or in combination produce one or more additional processed signals, to additionally control the controlled device of the present invention or to control one or more additional controlled devices.

In an alternative, preferred configuration of implanted components, a discrete component such as a sensor of the present invention is implanted within the cranium of the patient, such as sensor 200 of FIG. 2, a processing unit or a portion of the processing unit is implanted in the torso of the patient, and one or more discrete components are external to the body of the patient. The processing unit may receive multicellular signals from the sensor via wired (e.g., conductive wires and optic fibers) or wireless communication. The sensor 200 preferably includes signal processing means including signal processing up to and including digitizing the multicellular signals. In another alternative embodiment, for an acute (less than 24 hours) or sub-chronic (less than 30 days) application, for example, a through the skin, or transcutaneous device is used to transmit or enable the transmission of the multicellular signals and/or a derivative or pre-processed form of the multicellular signals.

Figure 3:
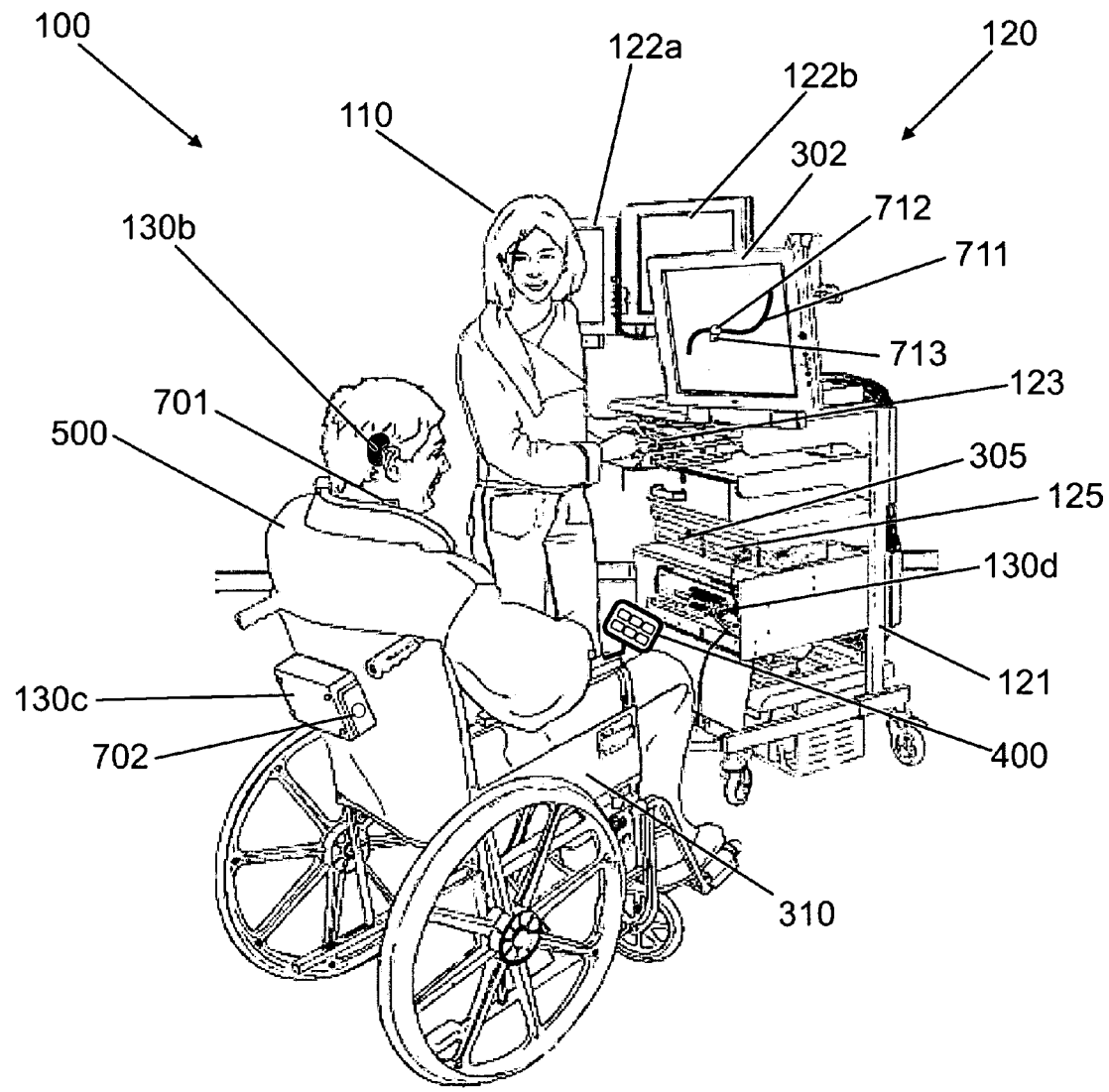
FIG. 3 illustrates another exemplary embodiment of a biological interface system consistent with the present invention wherein an operator configures the system at the patient site.

As shown in FIG. 3, a biological interface system 100 may comprise implanted components (not shown) and components external to the body of a patient 500. A sensor for detecting multicellular signals, preferably a two dimensional array of multiple protruding electrodes, has been implanted in the brain of patient 500, in an area such as the motor cortex. In a preferred embodiment, the sensor is placed in an area to record multicellular signals that are under voluntary control of the patient. Alternatively or additionally to the two dimensional array, the sensor may include one or more wires or wire bundles which include a plurality of electrodes. Patient 500 of FIG. 3 is shown as a human being, but other mammals and life forms that produce recordable multicellular signals would also be applicable. Patient 500 may be a patient with a spinal cord injury or afflicted with a neurological disease that has resulted in a loss of voluntary control of various muscles within the patient's body. Alternatively or additionally, patient 500 may have lost a limb, and system 100 will include a prosthetic limb as its controlled device. Numerous types of patients, including healthy individuals, are applicable to the system of the present invention. The patient of the present invention may be a quadriplegic, a paraplegic, an amputee, a spinal cord injury victim, or an otherwise physically impaired person. Alternatively or in addition, patient 500 may have been diagnosed with one or more of: obesity, an eating disorder, a neurological disorder, a psychiatric disorder, a cardiovascular disorder, an endocrine disorder, sexual dysfunction, incontinence, a hearing disorder, a visual disorder, sleeping disorder, a movement disorder, a speech disorder, physical injury, migraine headaches, or chronic pain. System 100 can be used to treat one or more medical conditions of patient 500, or to restore, partially restore, replace or partially replace a lost function of patient 500.

Alternatively, system 100 can be utilized by patient 500 to enhance performance, such as, for example, if patient 500 did not have a disease or condition from which a therapy or restorative device could provide benefit, but did have an occupation wherein thought control of a device provided an otherwise unachieved advancement in healthcare, crisis management and national defense. Thought control of a device can be advantageous in numerous healthy individuals including but not limited to: a surgeon, such as an individual surgeon using thought control to maneuver three or more robotic arms in a complex laparoscopic procedure or a surgeon controlling various instruments at a location remote from the instruments and the surgical procedure; a crisis control expert, such as a person who in attempting to minimize death and injury uses thought control to communicate different pieces of information and/or control multiple pieces of equipment, such as urban search and rescue equipment, simultaneously during an event such as an earthquake or other disaster, both natural disasters and those caused by man; a member of a bomb squad, such as an expert who uses thoughts to control multiple robots and/or robotic arms to remotely diffuse a bomb; and military personnel who uses thought control to communicate with other personnel and control multiple pieces of defense equipment, such as artillery, aircraft, watercraft, land vehicles, and reconnaissance robots. It should be noted that the above advantages of system 100 to a healthy individual are also advantages achieved in a patient such as a quadriplegic or paraplegic. In other words, a quadriplegic could provide significant benefit to society, such as in controlling multiple bomb diffusing robots, in addition to his or her own ambulation and other quality of life devices. Patients undergoing implantation and use of the system 100 of the present invention may provide numerous occupational and other functions not available to individuals that do not have the biological interface system of the present invention.

The sensor electrodes of system 100 can be used to detect various multicellular signals as has been described in detail in reference to FIG. 2 hereabove. The sensor is connected via a multi-conductor cable, implanted in patient 500, to an implanted portion of the processing unit (e.g., processing unit first portion 130a) which includes some signal processing elements as well as wireless communication means as has been described in detail in reference to FIG. 2. The implanted multi-conductor cable preferably includes a separate conductor for each electrode, as well as additional conductors to serve other purposes, such as providing reference signals and ground. A processing unit second portion 130b receives the wireless communications from the implanted portion. Processing unit second portion 130b is removably located just above ear 280 of patient 500, such as to be aligned with an infrared data transmission element of the implanted device. Multicellular signals or derivatives of the multicellular signals are transmitted from the implanted processing unit to processing unit second portion 130b for further processing. The processing unit components of system 100 perform various signal processing functions as have been described in detail in reference to FIG. 2. The processing unit may process signals that are mathematically combined, such as combining neuron spikes that are first separated using spike discrimination methods. In alternative embodiments, the processing unit may comprise multiple components or a single component. Each of the processing unit components can be fully implanted in patient 500, be external to the body, or be implanted with a portion of the component exiting through the skin.

In FIG. 3, a first controlled device is a computer including CPU 305 that may be attached to monitor 302 and integrated into configuration cart 121. Through the use of system 100, patient 500 can control one or more computer functions including but not limited to: an on/off function, a reset function, a language function, a modem function, a printer function, an Internet function, a cursor, a keyboard, a joystick, a trackball or other input device. Each function may be controlled individually or in combination. System 100 includes a second controlled device (e.g., wheelchair 310). Numerous other controlled devices can be included in the systems of this application, individually or in combination, including but not limited to: a computer; a computer display; a mouse; a cursor; a joystick; a personal data assistant; a robot or robotic component; a computer controlled device; a teleoperated device; a communication device or system; a vehicle such as a wheelchair; an adjustable bed; an adjustable chair; a remote controlled device; a Functional Electrical Stimulator device or system; a muscle stimulator; an exoskeletal robot brace; an artificial or prosthetic limb; a vision enhancing device; a vision restoring device; a hearing enhancing device; a hearing restoring device; a movement assist device; medical therapeutic equipment such as a drug delivery apparatus; medical diagnostic equipment such as epilepsy monitoring apparatus; other medical equipment such as a bladder control device, a bowel control device and a human enhancement device; closed loop medical equipment and other controllable devices applicable to patients with some form of paralysis or diminished function as well as any device that may be utilized under direct brain or thought control in either a healthy or unhealthy patient.

Processing unit second portion 130b includes a unique electronic ID, such as a unique serial number or any alphanumeric or other retrievable, identifiable code associated uniquely with the system 100 of patient 500. The unique electronic identifier may take many different forms in processing unit second portion 130b, such as, for example, a piece of electronic data stored in a memory module; a semiconductor element or chip that can be read electronically via serial, parallel or telemetric communication; pins or other conductive parts that can be shorted or otherwise connected to each other or to a controlled impedance, voltage or ground, to create a unique code; pins or other parts that can be masked to create a binary or serial code; combinations of different impedances used to create a serial code that can be read or measured from contacts, features that can be optically scanned and read by patterns and/or colors; mechanical patterns that can be read by mechanical or electrical detection means or by mechanical fit, a radio frequency ID or other frequency spectral codes sensed by radiofrequency or electromagnetic fields, pads and/or other marking features that may be masked to be included or excluded to represent a serial code, or any other digital or analog code that can be retrieved from the discrete component.

Alternatively or in addition to embedding the unique electronic ID in processing unit second portion 130b, the unique electronic ID can be embedded in one or more implanted discrete components. Under certain circumstances, processing unit second portion 130b or another external or implanted component may need to be replaced, temporarily or permanently. Under these circumstances, a system compatibility check between the new component and the remaining system components can be confirmed at the time of the repair or replacement surgery through the use of the embedded unique electronic ID. The unique electronic ID can be embedded in one or more of the discrete components at the time of manufacture, or at a later date such as at the time of any clinical procedure involving the system, such as a surgery to implant the sensor electrodes into the brain of patient 500. Alternatively, the unique electronic ID may be embedded in one or more of the discrete components at an even later date such as during a system configuration routine (e.g., a calibration routine).

Processing unit second portion 130b communicates with one or more discrete components of system 100 via wireless communication means. Processing unit second portion 130b communicates with selector module 400, a component utilized to select the specific device or devices to be controlled by the processed signals of system 100. Selector module 400 includes a touch screen set of buttons, input element 402, used to perform the selection process. Processing unit second portion 130b also communicates with controlled device CPU 305, such as to control a cursor, joystick, keyboard or other function of CPU 305. Processing unit second portion 130b further communicates with processing unit third portion 130c. Processing unit third portion 130c provides additional signal processing functions, as have been described above, to control wheelchair 310. An additional processing unit discrete component (e.g., processing unit fourth portion 130d)

may be included to perform additional processing of the multicellular signals and/or derivatives of these processed signals and/or processing of additional information, such as collective processing used to control one or more additional controlled devices of the present invention. System 100 may utilize selector module 400 to select one or more of CPU 305, wheelchair 310, or another controlled device to be controlled by the processed signals produced by the processing unit of the present invention. In system 100 of FIG. 3, one set of processed signals emanate from one portion of the processing unit (e.g., processing unit second portion 130b) and a different set of processed signals emanate from a different portion of the processing unit (e.g., processing unit third portion 130c).

The various components of system 100 communicate with wireless transmission means. However, it should be appreciated that physical cables can be used to transfer data alternatively or in addition to wireless means. These physical cables may include electrical wires, optical fibers, sound wave guide conduits, other physical means of transmitting data, and/or power, and any combination of those means.

A qualified individual, such as an operator 110 in cooperation with patient 500, is performing a patient training routine, one of numerous configuration programs or routines of the system. In an alternative embodiment, patient 500 is the operator of the patient training routine or other configuration routine. The patient training routine may be performed with controlled device 305. Displayed on monitor 302 is planned trajectory 711, system controlled target 712 and patient controlled object 713. In the performance of the patient training routine, multiple time varying stimulus, such as a moving system controlled target 712 are provided to the patient such that the patient can imagine moving that target, and a set of multicellular signals can be collected by the processing unit to produce one or more algorithms to produce the processed signals. In a preferred embodiment, after a first set of multicellular signals is collected, and a first transfer function for producing processed signals is developed, a second set of time varying stimulus is provided in combination with a patient controlled object, such as patient controlled object 713. During the time that the patient tries to mimic the motion of the system controlled target 712 with the visual feedback of the patient controlled target 713, and a second set of multicellular signals is collected and a second, improved transfer function is produced by the system. Additional forms of feedback can be provided to the patient, such as tactile transducer 701 shown attached to patient 500's neck, and speaker 702 shown attached (e.g., fixedly mounted to the back of controlled wheelchair 310) to processing unit third portion 130c. Speaker 702 and tactile transducer 701 can provide feedback in the form of a time varying stimulus, a derivative of the multicellular signals, and/or a representation of the processed signals as controlled by patient 500.

In an embodiment, one or more system configuration routines can be performed without an operator, with the patient as the operator, or with an operator at a remote location such as when the system of the present invention is electronically connected with a computer or computer network such as the Internet. In another embodiment, the patient training routine is performed at least one time during the use of the system, preferably before patient 500 is given, by the system, full control of one or more controlled devices. For example, limited control of CPU 305 may include the ability to send and receive email but not the ability to adjust a computer-controlled thermostat. Limited control of wheelchair 310 may be to turn left or right, but not move forward or back, or to only allow travel at a limited velocity. Limited control may also include no control of one or more controlled devices. Each controlled device will have different parameters limited by system 100 when patient 500 has not been given full control. In an embodiment, the selection of these parameters, the values to be limited, the criteria for achieving full control such as the value of a success threshold achieved during a system configuration routine such as a patient training routine, and any combinations of these may be modified only in a secured way such as only by a clinician utilizing electronic or mechanical keys or passwords.

In addition to successful completion of the patient training routine, completion of one or more other configuration routines may be required for patient 500 to have full control of one or more controlled devices, or multiple successful completions of a single routine. Success is preferably measured through the measurement of one or more performance parameters during or after the configuration routine. Success will be achieved by a performance parameter being above a threshold, such as a threshold adjustable only by a clinician, such as a clinician at a remote site utilizing a password, user identification, an electronic ID and/or a mechanical key. These configuration routines are utilized by the system to not only determine the applicability of full control to the patient, but to set or reset one or more system configuration parameters. System configuration parameters include but are not limited to: selection of cellular signals for processing by the processing unit; criteria for the selection of cells for processing; a coefficient of a signal processing function such as amplification, filtering, sorting, conditioning, translating, interpreting, encoding, decoding, combining, extracting, sampling, multiplexing, analog to digital converting, digital to analog converting, mathematically transforming; a control signal transfer function parameter such as a transfer function coefficient, algorithm, methodology, mathematical equation, a calibration parameter such as calibration frequency; a controlled device parameter such as a controlled device boundary limit; acceptable frequency range of cellular activity; selection of electrodes to include; selection of cellular signals to include; type of frequency analysis such as power spectral density; instruction information to patient such as imagined movement type or other imagined movement instruction; type, mode or configuration of feedback during provision of processed signal to patient; calibration parameter such as calibration duration and calibration frequency; controlled device parameter such as controlled device mode; alarm or alert threshold; and a success threshold.

As depicted in FIG. 3, operator 110 utilizes configuration apparatus 120 which includes two monitors (first configuration monitor 122a and second configuration monitor 122b), configuration keyboard 123, and configuration CPU 125, to perform a calibration routine or other system configuration process such as a patient training routine, algorithm and algorithm parameter selection and output device setup. The configuration routines, such as the patient training routine, include software programs and hardware required to perform the configuration. The embedded software and/or hardware may be included in the processing unit, such as processing unit second portion 130b, be included in selector module 400, be incorporated into configuration apparatus 120, a controlled device, or combinations of these. Configuration apparatus 120 may include additional input devices, such as a mouse or joystick, or an input device for a patient with limited motion, such as a tongue switch; a tongue palate switch; a chin joystick; a Sip-n-puff joystick controller; an eye tracker device; a head tracker device; an EMG switch such as an eyebrow EMG switch; an EEG activated switch; and a speech recognition device.

Configuration apparatus 120 may include various elements, functions, and data including but not limited to: memory storage for future recall of configuration activities, operator qualification routines, standard human data, standard synthesized or artificial data, neuron spike discrimination software, operator security and access control, controlled device data, wireless communication means, remote (such as via the Internet) configuration communication means and other elements, functions and data used to provide an effective and efficient configuration on a broad base of applicable patients and a broad base of applicable controlled devices. A system electronic ID can be embedded in one or more of the discrete components at the time, including an ID embedded at the time of system configuration. In an alternative embodiment, all or part of the functionality of configuration apparatus 120 is integrated into selector module 400 such that system 100 can perform one or more configuration processes such as a calibration procedure or patient training routine, utilizing selector module 400 without the availability of configuration apparatus 120.

In order to change a system configuration parameter, system 100 includes a permission routine, such as an embedded software routine or software driven interface that allows the operator to view information and enter data into one or more components of system 100. The data entered must signify an approval of the parameter modification in order for the modification to take place. Alternatively, the permission routine may be partially or fully located in a separate device such as configuration apparatus 120 of FIG. 3, or a remote computer such as a computer that accesses system 100 via the Internet or utilizing wireless technologies. In order to access the permission routine, and/or approve the modification of the system configuration parameters, a password or security key, mechanical, electrical, electromechanical or software based, may be required of the operator. Multiple operators may be needed or required to approve a parameter modification. Each specific operator or operator type may be limited by system 100, via passwords and other control configurations, to approve the modification of only a portion of the total set of modifiable parameters of the system. Additionally or alternatively, a specific operator or operator type may be limited to only approve a modification to a parameter within a specific range of values, such as a range of values set by a clinician when the operator is a family member. Operator or operator types, hereinafter operator, include but are not limited to: a clinician, primary care clinician, surgeon, hospital technician, system 100 supplier or manufacturer technician, computer technician, family member, immediate family member, caregiver, and patient.

In a preferred embodiment, the system 100 of FIG. 3 includes an interrogation function, which interrogates the system to retrieve certain information such as on the demand of an operator. Based on the analysis of the information, a recommendation for a parameter value change can be made available to the operator, such as by automatic configuration or calibration routines that are initiated by the operator initiated interrogation function. After viewing the modification, the appropriate operator would approve the change via the permission routine, such as using a computer mouse to click "OK" on a confirmation box displayed on a display monitor, or a more sophisticated, password controlled methodology.

In a preferred embodiment, an automatic or semi-automatic configuration function or routine is embedded in system 100. This embedded configuration routine can be used in place of a configuration routine performed manually by operator 110 as is described hereabove, or can be used in conjunction with one or more manual configurations. Automatic and/or semi-automatic configuration triggering event or causes can take many forms including but not limited to: monitoring of cellular activity, wherein the system automatically changes which particular signals are chosen to produce the processed signals; running parallel algorithms in the background of the one or more algorithms currently used to create the processed signals, and changing one or more algorithms when improved performance is identified in the background event; monitoring of one or more system functions, such as alarm or warning condition events or frequency of events, wherein the automated system shuts down one or more functions and/or improves performance by changing a relevant variable; and other methods that monitor one or more pieces of system data, identify an issue or potential improvement, and determine new parameters that would reduce the issue or achieve an improvement.

In an exemplary embodiment, when specific system configuration parameters are identified, by an automated or semi-automated calibration or other configuration routine, to be modified for the reasons described above, an integral permission routine of the system requires approval of a specific operator when one or more of the system configuration parameters are modified.

Operator 110 may be a clinician, technician, caregiver, patient family member or even the patient themselves in some circumstances. Multiple operators may be needed or required to perform a configuration routine or approve a modification of a system configuration parameter, and each operator may be limited by system 100, via passwords and other control configurations, to only perform or access specific functions. For example, only the clinician may be able to change specific critical parameters, or set upper and lower limits on other parameters, while a caregiver, or the patient, may not be able to access those portions of the configuration procedure or the permission procedure. The configuration routine includes the setting of numerous parameters needed by system 100 to properly control one or more controlled devices. The parameters include but are not limited to various signal conditioning parameters as well as selection and de-selection of specific multicellular signals for processing to generate the device control creating a subset of signals received from the sensor to be processed. The various signal conditioning parameters include, but are not limited to: threshold levels for amplitude sorting, other sorting and pattern recognition parameters, amplification parameters, filter parameters, signal conditioning parameters, signal translating parameters, signal interpreting parameters, signal encoding and decoding parameters, signal combining parameters, signal extracting parameters, mathematical parameters including transformation coefficients and other signal processing parameters used to generate a control signal for transmission to a controlled device.

The configuration routine will result in the setting of various system configuration output parameters, all such parameters to be considered system configuration parameters. Configuration output parameters may include but be not limited to: electrode selection, cellular signal selection, neuron spike selection, electrocorticogram signal selection, local field potential signal selection, electroencephalogram signal selection, sampling rate by signal, sampling rate by group of signals, amplification by signal, amplification by group of signals, filter parameters by signal and filter parameters by group of signals. In a preferred embodiment, the configuration output parameters are stored in memory in one or more discrete components, and the parameters are linked to the system's unique electronic ID.

Calibration, patient training, and other configuration routines, including manual, automatic and semi-automatic routines, may be performed on a periodic basis, and may include the selection and deselection of specific cellular signals over time. The initial configuration routine may include initial values, or starting points, for one or more of the configuration output parameters. Setting initial values of specific parameters, may invoke a permission routine. Subsequent configuration routines may involve utilizing previous configuration output parameters that have been stored in a memory storage element of system 100. Subsequent configuration routines may be shorter in duration than an initial configuration and may require less patient involvement. Subsequent configuration routine results may be compared to previous configuration results, and system 100 may require a repeat of configuration if certain comparative performance is not achieved.

The configuration routine may include: (a) setting a preliminary set of configuration output parameters; (b) generating processed signals to control the controlled device; (c) measuring the performance of the controlled device control; and (d) modifying the configuration output parameters. The configuration routine may further include the steps of repeating steps (b) through (d). The configuration routine may also require invoking a permission routine.

In the performance of a configuration routine, the operator 110 may involve patient 500 or perform steps that do not involve the patient. In the patient training routine and other routines, the operator 110 may have patient 500 imagine one or more particular movements, imagined states, or other imagined events, such as a memory, an emotion, the thought of being hot or cold, or other imagined event not necessarily associated with movement. The patient participation may include: the patient training routine providing one or more time varying stimulus, such as audio cues, visual cues, olfactory cues, tactile cues, moving objects on a display such as a computer screen, moving mechanical devices such as a robotic arm or a prosthetic limb, moving a part of the patient's body such as with an exoskeleton or FES implant, changing audio signals, changing electrical stimulation such as cortical stimulation, moving a vehicle such as a wheelchair or car; moving a model of a vehicle; moving a transportation device; and other sensory stimulus. The imagined movements may include the imagined movement of a part of the body, such as a limb, arm, wrist, finger, shoulder, neck, leg, angle, and toe, as well as imagining moving to a location, moving in a direction, moving at a velocity or moving at an acceleration.

The patient imagines moving system controlled target 712 along planned trajectory 711, as target 712 is moving as controlled by the system or manually by operator 110. The current processed signal, hereinafter a representation of the processed signal, available by applying a transfer function to the multicellular signals detected during the imagined movement or other step of the patient training routine, is displayed in the form of control of patient controlled target 713. The transfer function is preferably based on multicellular signals stored during a previous imagined movement, or multiple previous imagined movements, preferably two or more sets of states of time varying stimulus. The representation of the processed signal may mimic the time varying stimulus, similar to patient controlled object 713 being a similar form to system controlled object 712.

Alternatively, the time varying stimulus and representation of the processed signals may take different forms, such as a time varying stimulus including an object on a visual display, wherein the representation is a moving mechanical structure, or the stimulus being a moving mechanical structure and the representation comprising an object on a visual display. The representation of the processed signals can be provided to the patient in visual form such as a visual representation of limb motion displayed on a computer monitor, or in one or more sensory forms such as auditory, olfactory, gustatory, and electrical stimulation such as cortical stimulation. The representation of the processed signals can be provided in combinations of these and other forms.

In some exemplary embodiments, the first patient training step may not include patient controlled object 713, or it may include a patient controlled target whose processed signal is not based on a set of multicellular signals collected during a previous imagined movement. Multiple steps of providing a set of states of the time varying stimulus and recording the multicellular signal data may involve different subsets of cells from which the multicellular signals are detected. Also, different sets of states of time varying stimulus may have different numbers of cells in each. Alternative to the system controlled target 712 along planned trajectory 711, the patient may imagine movements while viewing a time varying stimulus comprising a video or animation of a person performing the specific movement pattern. In a preferred embodiment, this visual feedback is shown from the patient's perspective, such as a video taken from the person performing the motion's own eye level and directional view. Multiple motion patterns and multiple corresponding videos may be available to improve or otherwise enhance the patient training process. The patient training routine temporally correlates a set of states of the time varying stimulus with the set of multicellular signal signals captured and stored during that time period, such that a transfer function can be developed for future training or controlled device control. Correlations can be based on numerous variables of the motion including but not limited to: position, velocity and acceleration of the time varying stimulus; a patient physiologic parameter such as heart rate; a controlled device parameter; a system environment parameter; a password controlled parameter; a clinician controlled parameter; and a patient training routine parameter. In the patient training routine of FIG. 3, the controlled device, CPU 305 and controlled monitor 302 are used in the patient training routine to display the time varying stimulus as well as the representation of the processed signal. In a subsequent step, wheelchair 310 can also be employed, such as by a system controlling the wheelchair while the patient imagines the control, the wheelchair movement being the time varying stimulus.

During the time period that a set of states of the time varying stimulus is applied, multicellular signal data detected by the implanted sensor is stored and temporally correlated to that set of states of the time varying stimulus provided to the patient. In a preferred embodiment, the system of the present invention includes a second patient training routine and a second controlled device, wherein the first patient training routine is used to configure the first controlled device and the second patient training routine is used to configure the second controlled device. The two patient training routines may include different time varying stimulus, chosen to optimize the routine for the specific controlled device, such as a moving cursor for a computer mouse control system, and a computer simulated prosthetic limb for a prosthetic limb control system. In a preferred system, the first controlled device is a prosthetic arm and the second controlled device is a prosthetic leg, this system having two different time varying stimulus in the two corresponding patient training routines.

In one embodiment, the first controlled device is a prosthetic arm and the second controlled device is a wheelchair. This system may also have two different time varying stimulus in the two corresponding patient training routines. In an alternative, preferred embodiment, a controlled device surrogate is utilized in the patient training routine. The controlled device surrogate preferably has a larger value of one or more of: degrees of freedom; resolution; modes; discrete states; functions; and boundary conditions. Numerous boundary conditions with greater values for the surrogate device can be employed. Such boundary conditions may include: maximum distance; maximum velocity; maximum acceleration; maximum force; maximum torque; rotation; and position. The surrogate device employing larger values of these parameters creates the scenario wherein the patient is trained and/or tested with a device of more complexity than the eventual controlled device to be used.

The time varying stimulus may be supplied to the patient in numerous forms such as visual, tactile, olfactory, gustatory, and electrical stimulation such as cortical stimulation. The time varying stimulus may be moved around manually, automatically produced and controlled by a component of the system such as the processing unit, or produced by a separate device. The time varying stimulus may include continuous or semi-continuous motion of an object, such as an object moving on a visual display, a mechanical object moving in space, or a part of the patient's body moving in space. The time varying stimulus may be of a short duration, such as an object appearing and disappearing quickly on a display, or a flash of light.

In an embodiment, the patient training routine includes multiple forms of feedback, in addition to the time varying stimulus, such feedback provided to the patient in one or more forms including but not limited to: visual; tactile; auditory; olfactory; gustatory; and electrical stimulation. The additional feedback may be a derivative of the multicellular signals, such as visual or audio feedback of one or more neuron spike modulation rates. Different forms of feedback may be provided as based on a particular device to be controlled by the processed signals. Numerous parameters for the time varying stimulus and other feedback may be adjustable, such as by an operator such as the patient. These parameters including but not limited to: sound volume and frequency; display brightness, contrast, size and resolution; display object size; electrical current parameter such as current or voltage; mechanical or visual object size, color, configuration, velocity or acceleration; and any combinations of these.

A configuration routine such as a calibration or patient training routine may utilize one or more configuration input parameters to determine one or more system output parameters used to develop a processed signal transfer function. In addition to the multicellular signals themselves, system or controlled device performance criteria can be utilized. Other configuration input parameters include various properties associated with the multicellular signals including one or more of: signal to noise ratio, frequency of signal, amplitude of signal, neuron firing rate, average neuron firing rate, standard deviation in neuron firing rate, modulation of neuron firing rate as well as a mathematical analysis of any signal property including but not limited to modulation of any signal property. Additional configuration input parameters include but are not limited to: system performance criteria, controlled device electrical time constants, controlled device mechanical time constants, other controlled device criteria, types of electrodes, number of electrodes, patient activity during configuration, target number of signals required, patient disease state, patient condition, patient age and other patient parameters and event based (such as a patient imagined movement event) variations in signal properties including neuron firing rate activity. In a preferred embodiment, one or more configuration input parameters are stored in memory and linked to the embedded, specific, unique electronic identifier. All configuration input parameters shall be considered a system configuration parameter of the system.

In some exemplary embodiments, it may be desirous for the configuration routine to exclude one or more multicellular signals based on a desire to avoid signals that respond to certain patient active functions, such as non-paralyzed functions, or even certain imagined states. The configuration routine may include having the patient imagine a particular movement or state, and based on sufficient signal activity such as firing rate or modulation of firing rate, exclude that signal from the signal processing based on that particular undesired imagined movement or imagined state. Alternatively real movement accomplished by the patient may also be utilized to exclude certain multicellular signals emanating from specific electrodes of the sensor. In a preferred embodiment, an automated or semi-automated calibration or other configuration routine may include through addition, or exclude through deletion, a signal based on insufficient activity during known patient movements.

The configuration routines of the system of the present invention, such as a patient training routine in which a time varying stimulus is provided to the patient, may conduct adaptive processing, such as adapting between uses or within a single patient training routine. The adaptation may be caused by a superior or inadequate level of performance, as compared to a threshold, such as an adjustable threshold. In a preferred embodiment, performance during a patient training routine above a threshold causes the duration of the routine to decrease, and performance below a threshold causes the duration of the routine to increase. Control of the controlled device or surrogate controlled device is a preferred way of measuring performance. Alternatively, a change in multicellular signals, such as a change in modulation rate may cause an adaptation to occur. A monitored difference is a first patient training event and a second patient training event, such as a difference in signal modulation, may cause an adaptation in the patient training routine, such as to preferentially choose one time varying stimulus over another time varying stimulus. Other causes include a change to a patient parameter, such as the level of patience consciousness. In a preferred embodiment, at a low level of consciousness, the patient training routine changes or discontinues. The level of consciousness may be determined by the multicellular signals detected by the sensor. Alternatively, the level of consciousness can be detected utilizing a separate sensor, such as a sensor to detect EEG or LFP signals. The patient training routine may automatically adapt, such as due to a calculation performed by the processing unit, or may adapt due to operator input.

In an exemplary embodiment, the system may include a processing unit that processes multicellular signals received from patient 500. Processing unit second portion 130*b* and other processing unit components, singly or in combination, perform one or more functions. The functions performed by the processing unit include but are not limited to: producing the processed signals; transferring data to a separate device; receiving data from a separate device; producing processed signals for a second controlled device; activating an alarm, alert or warning; shutting down a part of or the entire system; ceasing control of a controlled device; storing data; and performing a configuration.

In order for the processing unit of system 100 to perform one or more functions, one or more system configuration parameters are utilized. These parameters include pieces of data stored in, sent to, or received from, any component of system 100, including but not limited to: the sensor; a processing unit component; processing unit second portion 130*b*; or a controlled device. Parameters can be received from devices outside of system 100 as well, such as configuration apparatus 120, a separate medical therapeutic or diagnostic device, a separate Internet based device, or a separate wireless device. These parameters can be numeric or alphanumeric data, and can change over time, either automatically or through an operator involved configuration or other procedure.

The processing unit, or other component of system 100 may produce multiple processed signals for controlling one or more controlled device. This second processed signal may be based on multicellular signals of the sensor, such as the same set of cells as the first processed signal is based on, or a different set of cells emanating signals. The signal processing used to produce the additional processed signals can be the same as the first, or utilize different processing, such as different transfer functions. Transfer functions may include different algorithms, coefficients such as scaling factors, different types of feedback, and other transfer function variations. Alternatively, the additional processed signals may be based on signals not received from the sensor in which the first processed signal is derived. An additional sensor, such as a similar or dissimilar sensor, may provide the signals to produce the additional processed signals, or the system may receive a signal from an included input device such as a tongue switch; tongue palate switch; chin joystick; Sip-n-puff joystick controller; eye gaze tracker; head tracker; EMG switch such as eyebrow EMG switch; EEG activated switch; speech recognition device; and any combinations thereof. The additional processed signal may be derived from a monitored biological signal such as a signal based on eye motion; eyelid motion; facial muscle activation or other electromyographic activity; heart rate; EEG; LFP; respiration; and any combinations thereof. In creating the additional processed signal or signals, the processing unit may convert these alternative input signals into a digital signal, such as a digital signal used to change the state of the system, such as a change in state of an integrated configuration routine.

Figure 4A:
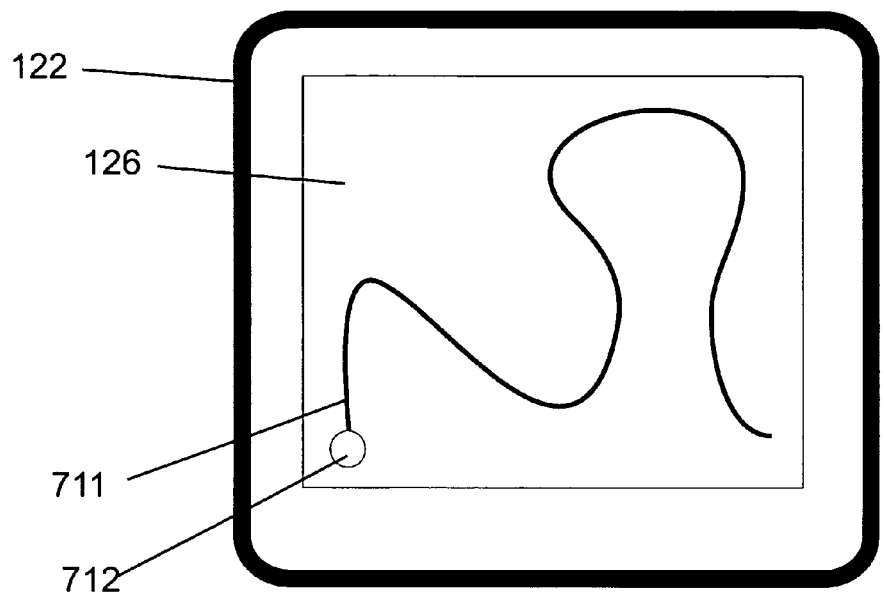
FIG. 4a illustrates a patient training display with a time varying stimulus and a predictory path consistent with the present invention.
Figure 4B:
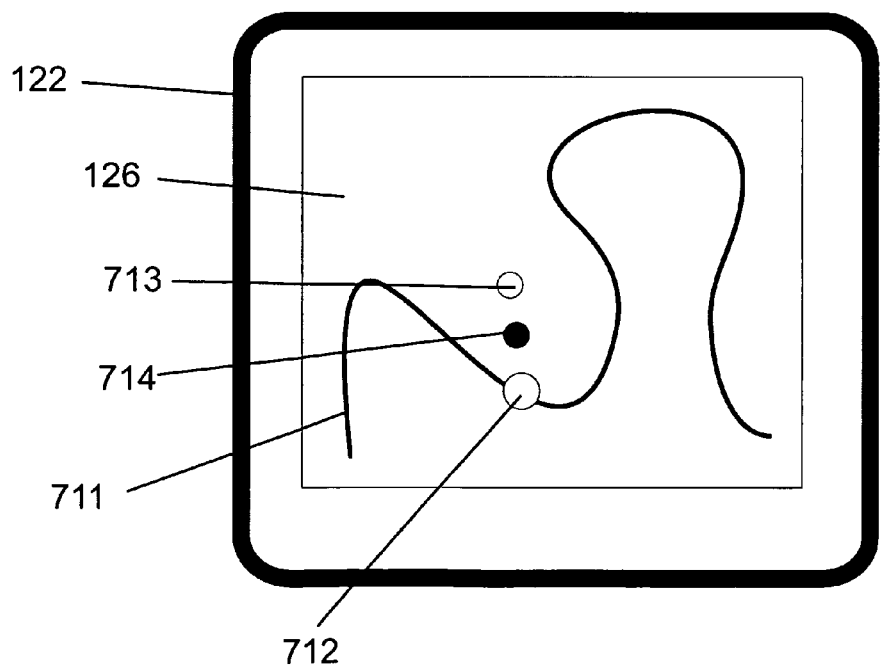
FIG. 4b illustrates the patient training display of FIG. 4a further depicting a patient controlled object and a modified patient controlled object.

Referring now to FIGS. 4*a* and 4*b*, a patient training display depicting a time varying stimulus and predictory path is illustrated. FIG. 4*a* shows a time varying stimulus comprising target 712 within a display area 126 on configuration monitor 122. In the patient training routine of the present invention, target 712 will move, at a constant or non-constant rate, along predictory path 711. Target 712 may be moved around manually, such as by an operator of the system, preferably not the patient. The target may be controlled without operator input, such as by the processing unit of the system. Alternatively, a separate device, such as a configuration system, can be used during the patient training routine and control target 712. The target will assume a set of states that result in continuous or semi-continuous motion of target 712.

Referring specifically to FIG. 4*b*, target 712 has moved along trajectory path 711 such as in the middle of a patient training routine step. Also depicted are two more forms of feedback to the patient, patient controlled object 713, and modified patient controlled object 714. Patient controlled object 713 is an icon or other screen object that is moved within display area 126 by the representation of processed signals as described in detail in reference to FIG. 1. Modified patient controlled object 714 is moved within display area 126 by a modified representation of processed signals, such as a modification with a bias toward target 712, such as shown by object 714 being closer to target 712 than object 713. In a preferred embodiment, the amount of bias improvement used decreases as the patient's actual performance increases. In addition to, or alternative to object 713 and object 714, the patient may receive feedback in the form of: moving mechanical device such as a mechanical limb or wheelchair; moving part of patient's body such as via an exoskeleton device or FES device; changing audible signal such as a multi-frequency signal; and any combinations thereof. The patient may also receive a feedback that represents the difference between a desired level of control, and an actual or achieved level of control.

In an alternative embodiment, a competitive user routine is included in the system of the present invention. A competitive routine is activated to provide a competitive function for the patient during the patient training task. The function may allow an operator to also attempt to track target 712. Alternatively, the system itself may provide a competitive function, such as a competitive software algorithm which uses random values for parameters to create a competitive environment. In another preferred embodiment, a separate patient, such as a patient at a remote location in communication with the system of the present invention such as via a computer network such as the Internet, attempts to track target 712 with that patient's system including that patient's multicellular signals. For certain patients, such as patients who have competed in competitive sports prior to an accident causing their injury, a competitive function may help to improve the outcomes of one or more configuration routines of the system such as patient training routines.

Figure 5:
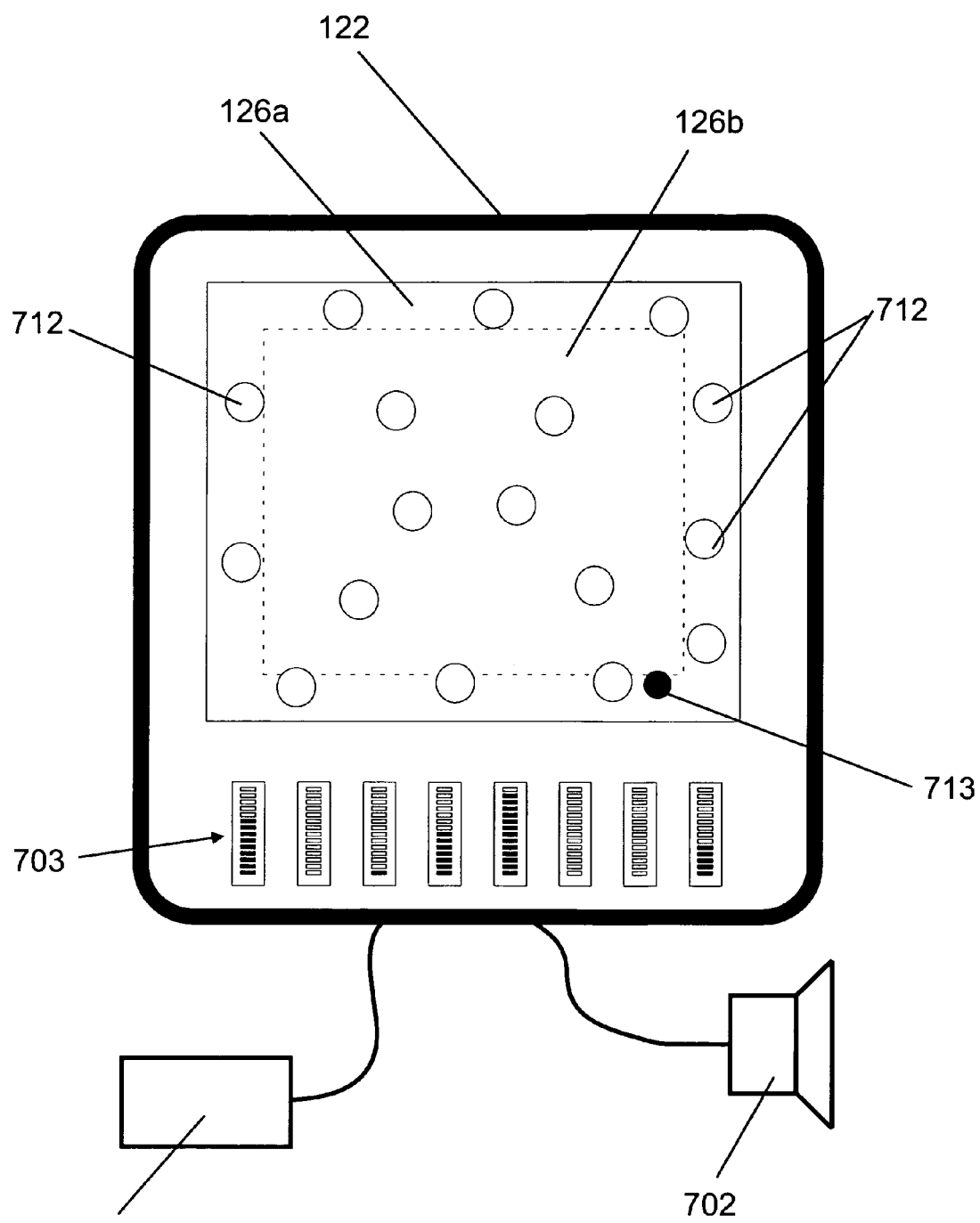
FIG. 5 illustrates a patient training display as well as feedback speakers and feedback tactile transducer, all consistent with the present invention.

Referring now to FIG. 5, a patient training display of the present invention is illustrated with additional feedback in the form of audio and tactile feedback. Configuration monitor 122, which is preferably the monitor of a computer that is also a controlled device of the system, includes a time varying stimulus comprising multiple targets 712 that are displayed as existing within a domain of values defined by first display area 126*a*. First display area 126*a* includes a set of values corresponding to a set of two-dimensional positions within first display area 126*a*. In an alternative embodiment, the set of values may correspond to three-dimensional positions wherein the third dimension is represented by varying one or more parameters of the object, such as color or size, or by adding additional feedback such as a sound that corresponds to the third dimensional coordinate. Targets 712 may appear sequentially, such as to have the patient imagine moving from one to the other. The targets may be sequentially numbered, sequentially change color, or include other sequence defining means.

After a first set of multicellular signals is collected simultaneous to the patient imagining movement from target to target, a representation of processed signals can be created, such as via the temporal correlation of the multicellular signals to set of states of the time varying stimulus. In a subsequent step, both the time varying stimulus and the patient controlled, via the representation of processed signals control of patient controlled object 713 while a second set of multicellular signals is collected and correlated. When the patient training routine is successfully completed, as has been described in detail hereabove in reference to FIG. 1, the patient may control an icon or cursor on the computer screen within an allowable range of values (e.g., second display area 126*b*). This allowable range of values with the set of positions defined by second display area 126*b*, is a subset of the domain of values defined by first display area 126*a*. In a preferred embodiment, the number of positions defined by the allowable range of values is at least ninety percent of the number of positions defined by the domain of values. After the patient training routine is completed, the computer screen can be adjusted, such as via a monitor configuration, such that the second display area 126*b* fills the entire screen. In an alternative embodiment, the patient training routine is performed at a higher screen resolution than the subsequent control of the computer.

The components of the system of FIG. 5 providing the patient training routine further include speaker 702, such as to provide audio feedback to the patient, and tactile transducer 701, such as to provide tactile feedback to the patient, such as to the patient's neck or other body portion that has functional sensory feedback to the patient's brain. Speaker 702 and tactile transducer 701 can additionally or alternatively provide feedback in the form of the time varying stimulus of the patient training routine, or the representation of the processed signals also of the patient training routine. Numerous forms of feedback can be used for either or both of these purposes, such feedback forms including but not limited to: auditory; olfactory; gustatory; visual; electrical stimulation such as cortical stimulation; and any combinations thereof. Neural signal display 703, which may be an additional patient feedback, includes multiple bar graph meters which display derivatives of the multicellular signals, such as a level of modulation of one or more neurons of the patient's motor cortex, or other cellular signal parameter that can be quantified, or processed and quantified. The multiple forms of feedback can be used to help the patient prior to, during, or after an imagined movement or other imagined event, improve the quantity and or quality of the multicellular signals received from the sensor or sensors of the present invention.

While the components of FIG. 5 include a domain of values for the time varying stimulus and an allowable range of values for processed signal controlled objects that are represented by moveable objects on a visual display, other forms of time varying stimulus ranges can be utilized by the system of the present invention. In an alternative embodiment, a movable mechanical device can be moved through a set of positions in space. Alternatively, the system may incorporate for the time varying stimulus and/or the representation of processed signals one or more of the following: a set of sounds within a frequency range; a set of tactile forces or force patterns; a set of stimulation energies; or other varying feedback form that can exist within a domain of values wherein the allowable range of the controlled device processed signals is a subset of the domain of values. Devices used to represent either or both the time varying stimulus and the object controlled by the representation of processed signals preferably include: a human body part such as an FES driven limb; a prosthetic limb; a robotic mechanism such as a robotic arm; a vehicle such as a wheelchair, car or tank; moving or changing objects on a visual display; and any combinations thereof.

Numerous methods are provided in the multiple embodiments of the disclosed invention. An exemplary embodiment provides a patient training routine for a biological interface apparatus that must be performed by an operator. The biological interface system is for collecting multicellular signals emanating from one or more living cells of a patient and for transmitting processed signals to control a device. The biological interface system comprises: a sensor for detecting the multicellular signals, the sensor comprising a plurality of electrodes to allow for detection of the multicellular signals; a processing unit for receiving the multicellular signals from the sensor, for processing the multicellular signals to produce processed signals, and for transmitting the processed signals; a controlled device for receiving the processed signals; and a patient training routine for generating one or more system configuration parameters.

It should be understood that numerous other configurations of the systems, devices, and methods described herein could be employed without departing from the spirit or scope of this application. It should be understood that the system includes multiple functional components, such as a sensor for detecting multicellular signals, a processing unit for processing the multicellular signals to produce processed signals, and the controlled device that is controlled by the processed signals. Different from the logical components are physical or discrete components, which may include a portion of a logical component, an entire logical component and any combinations of portions of logical components and entire logical components. These discrete components may communicate or transfer information to or from each other, or communicate with devices outside the system. In each system, physical wires, such as electrical wires or optical fibers, can be used to transfer information between discrete components, or wireless communication means can be utilized. Each physical cable can be permanently attached to a discrete component, or can include attachment means to allow attachment and potentially allow, but not necessarily permit, detachment. Physical cables can be permanently attached at one end, and include attachment means at the other.

The sensors of the systems of this application can take various forms, including multiple discrete component forms, such as multiple penetrating arrays that can be placed at different locations within the body of a patient. The processing unit of the systems of this application can also be contained in a single discrete component or multiple discrete components, such as a system with one portion of the processing unit implanted in the patient, and a separate portion of the processing unit positioned external to the body of the patient. The sensors and other system components may be utilized for short term applications, such as applications less than twenty four hours, sub-chronic applications such as applications less than thirty days, and chronic applications. Processing units may include various signal conditioning elements such as amplifiers, filters, signal multiplexing circuitry, signal transformation circuitry and numerous other signal processing elements. In a preferred embodiment, an integrated spike sorting function is included. The processing units performs various signal processing functions including but not limited to: amplification, filtering, sorting, conditioning, translating, interpreting, encoding, decoding, combining, extracting, sampling, multiplexing, analog to digital converting, digital to analog converting, mathematically transforming and/or otherwise processing cellular signals to generate a control signal for transmission to a controllable device. The processing unit utilizes numerous algorithms, mathematical methods and software techniques to create the desired control signal. The processing unit may utilize neural net software routines to map cellular signals into desired device control signals. Individual cellular signals may be assigned to a specific use in the system. The specific use may be determined by having the patient attempt an imagined movement or other imagined state. For most applications, it is preferred that that the cellular signals be under the voluntary control of the patient. The processing unit may mathematically combine various cellular signals to create a processed signal for device control.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A biological interface system comprising:
a sensor comprising a plurality of electrodes for detecting multicellular signals emanating from two or more living cells of a patient;
a processing unit configured to receive the multicellular signals from the sensor and process the multicellular signals to produce a processed signal, the processing unit being configured to transmit the processed signal to a controlled device that is configured to receive the processed signal;
a surrogate of the controlled device for use during an integrated patient training routine, the surrogate configured to be more complex than the controlled device,
wherein the system is configured to perform the integrated patient training routine using the surrogate of the controlled device to generate one or more system configuration parameters that are used by the processing unit to produce the processed signal,
wherein the system is configured such that the patient training routine is performed at least once during use of the system,
wherein the system is configured to set a threshold value for determining the successful completion of the training routine, and
wherein less than full control of the controlled device is available to the patient prior to successful completion of the patient training routine.

2. The system of claim 1, wherein the patient training routine provides one or more time varying stimulus to the patient.

3. The system of claim 1, wherein the system is configured to allow an operator to perform the patient training routine.

4. The system of claim 3, wherein the operator comprises the patient.

5. The system of claim 1, further comprising a second controlled device, wherein the system is configured to perform a second patient training routine, and the second patient training routine is performed at least once during a use of the second controlled device.

6. The system of claim 1, wherein the one or more system configuration parameters comprise a calibration parameter.

7. The system of claim 1, wherein the system is configured to restore a patient function.

8. The system of claim 7, wherein the patient function comprises one or more of: vision; hearing; speech; communication; limb motion; ambulation; reaching; grasping; standing; sitting; rolling over; bowel movement; bladder evacuation; and any combination thereof.

9. The system of claim 1, wherein the multicellular signals comprise one or more of: neuron spikes, electrocorticogram (ECoG) signals, local field potential (LFP) signals, and electroencephalogram (EEG) signals.

10. The system of claim 1, wherein the sensor includes at least one multi-electrode array comprising the plurality of electrodes.

11. The system of claim 1, wherein the sensor transmits the multicellular signals through a wireless connection.

12. The system of claim 1, wherein the patient training routine utilities the controlled device.

13. The system of claim 1, wherein the threshold value is adjustable.

14. The system of claim 13, wherein the system is configured to allow a clinician to adjust the threshold value.

15. The system of claim 13, wherein the system is configured such that an adjustment to the threshold value is made from a remote location.

16. The system of claim 13, wherein the system is configured to perform a permission routine prior to an adjustment to the threshold value.

17. The system of claim 16, wherein the adjustment is controlled by one or more of: a password; a user identification; an electronic ID; and a mechanical key.

18. The system of claim 1, wherein the patient training routine provides a time varying stimulus to the patient.

19. The system of claim 1, wherein the system is configured to perform an adaptive processing routine.

20. The system of claim 19, wherein the adaptive processing routine includes changing over time the type or combination of types of signals processed.

21. The system of claim 20, wherein the types of signals processed include one or more of: electrocorticogram (ECoG) signals, local field potential (LFP) signals, electroencephalogram (EEG), and neural spikes.

22. The system of claim 1, wherein the controlled device comprises a piece of medical equipment.

23. The system of claim 1, further comprising a second controlled device.

24. The system of claim 1, wherein the patient training routine comprises a software program.

25. A biological interface system comprising:
a sensor comprising a plurality of electrodes for detecting multicellular signals emanating from two or more living cells of a patient;
a processing unit configured to receive the multicellular signals from the sensor and process the multicellular signals to produce a processed signal, the processing unit being configured to transmit the processed signal to a controlled device that is configured to receive the processed signal; and
a surrogate of the controlled device for use during an integrated rated patient training routine, the surrogate configured to be more complex than the controlled device,
wherein the system is configured to perform the integrated patient training routine using the surrogate of the controlled device to generate one or more system configuration parameters that are used by the processing unit to produce the processed signal, and
wherein the system is configured such that the patient training routine is performed at least once during use of the system.

26. The system of claim 25, wherein the patient training routine provides a time varying stimulus to the patient.

27. The system of claim 25, wherein the system is configured to allow an operator to perform the patient training routine.

28. The system of claim 27, wherein the operator comprises the patient.

29. The system of claim 25, wherein the patient training routine comprises a software program.

30. The system of claim 25, further comprising a second controlled device, wherein the system is configured to perform a second patient training routine, and the second patient training routine is performed at least once during a use of the second controlled device.

31. The system of claim 25, wherein the one or more system configuration parameters comprise a calibration parameter.

32. The system of claim 25, wherein the system is configured to restore a patient function.

33. The system of claim 32, wherein the patient function comprises one or more of: vision; hearing; speech; communication; limb motion; ambulation; reaching; grasping; standing; sitting; rolling over; bowel movement; bladder evacuation; and any combination thereof.

34. The system of claim 25, wherein the multicellular signals comprise one or more of: neuron spikes, electrocorticogram (ECoG) signals, local field potential (LFP) signals, and electroencephalogram (EEG) signals.

35. The system of claim 25, wherein the sensor includes at least one multi-electrode array comprising the plurality of electrodes.

36. The system of claim 25, wherein the sensor transmits the multicellular signals through a wireless connection.

37. The system of claim 25, wherein the controlled device comprises a piece of medical equipment.

* * * * *